(12) United States Patent
Doll et al.

(10) Patent No.: US 10,792,117 B2
(45) Date of Patent: Oct. 6, 2020

(54) SURGICAL INSTRUMENT

(71) Applicant: Karl Storz SE & Co. KG, Tuttlingen (DE)

(72) Inventors: Frank Doll, Tuttlingen (DE); Yann Thouément, Les Essarts le Roi (FR); Régis Besse, Le Perray-en-Yvelines (FR); Daniel Kärcher, Tuttlingen (DE); Marian Pfeffer, Tuttlingen (DE)

(73) Assignee: KARL STORZ SE & CO. KG, Tuttlingen (DE)

( * ) Notice: Subject to any disclaimer, the term of this patent is extended or adjusted under 35 U.S.C. 154(b) by 240 days.

(21) Appl. No.: 15/874,280

(22) Filed: Jan. 18, 2018

(65) Prior Publication Data

US 2018/0206928 A1 Jul. 26, 2018

(30) Foreign Application Priority Data

Jan. 20, 2017 (DE) .......................... 10 2017 101 093

(51) Int. Cl.
*A61B 34/00* (2016.01)
*A61B 10/06* (2006.01)
(Continued)

(52) U.S. Cl.
CPC .............. *A61B 34/71* (2016.02); *A61B 10/06* (2013.01); *A61B 17/29* (2013.01);
(Continued)

(58) Field of Classification Search
CPC ..... A61B 10/06; A61B 17/29; A61B 17/2909; A61B 17/3201; A61B 2017/314;
(Continued)

(56) References Cited

U.S. PATENT DOCUMENTS

| 5,618,306 A | 4/1997 | Roth et al. |
| 6,083,150 A | 7/2000 | Aznoian et al. |

(Continued)

FOREIGN PATENT DOCUMENTS

| DE | 196 08 809 A1 | 9/1997 |
| DE | 10 2006 040 529 A1 | 3/2008 |

(Continued)

OTHER PUBLICATIONS

Search Report, EP 18 152 174.1, dated May 24, 2018 (9 pgs.).

(Continued)

*Primary Examiner* — Shaun L David
*Assistant Examiner* — Mohamed G Gabr
(74) *Attorney, Agent, or Firm* — Eversheds Sutherland (US) LLP

(57) ABSTRACT

A surgical instrument comprises a shaft, wherein a deflectable articulation section is formed at the shaft, a proximal handling portion at a proximal end of the shaft, a distal effector at a distal end of the shaft, and a deflection mechanism for controlling a bending state of the articulation section. The deflection mechanism comprises a first pull element for a deflection movement and a second pull element for a return movement. The first pull element and the second pull element are jointly pretensioned during the movement of the articulation section. An interface is provided where the instrument is demountable into a distal shaft assembly and a proximal handle piece, wherein the effector is controlled via an actuation mechanism that passes through the interface in a mounted state. The actuation mechanism comprises a push piece having a distal end that is coupled with the effector and a proximal end that is actuable by a pushing movement.

23 Claims, 11 Drawing Sheets

(51) Int. Cl.
*A61B 17/29* (2006.01)
*A61B 17/3201* (2006.01)
*A61B 90/00* (2016.01)
*A61B 17/28* (2006.01)
*A61B 17/32* (2006.01)
*A61B 17/00* (2006.01)
*A61B 17/30* (2006.01)
*A61B 90/10* (2016.01)
*A61B 18/00* (2006.01)

(52) U.S. Cl.
CPC ...... *A61B 17/2909* (2013.01); *A61B 17/3201* (2013.01); *A61B 2017/0046* (2013.01); *A61B 2017/00314* (2013.01); *A61B 2017/00327* (2013.01); *A61B 2017/2808* (2013.01); *A61B 2017/2902* (2013.01); *A61B 2017/2915* (2013.01); *A61B 2017/2916* (2013.01); *A61B 2017/2919* (2013.01); *A61B 2017/2925* (2013.01); *A61B 2017/2932* (2013.01); *A61B 2017/2933* (2013.01); *A61B 2017/2934* (2013.01); *A61B 2017/2936* (2013.01); *A61B 2017/305* (2013.01); *A61B 2017/320008* (2013.01); *A61B 2018/00589* (2013.01); *A61B 2090/0813* (2016.02); *A61B 2090/103* (2016.02)

(58) Field of Classification Search
CPC .. A61B 2017/00327; A61B 2017/0046; A61B 2017/2808; A61B 2017/2902; A61B 2017/2915; A61B 2017/2916; A61B 2017/2919; A61B 2017/2925; A61B 2017/2932; A61B 2017/2933; A61B 2017/2934; A61B 2017/2936; A61B 2017/205; A61B 2017/320008; A61B 2018/00589; A61B 2090/0813; A61B 34/71
See application file for complete search history.

(56) References Cited

U.S. PATENT DOCUMENTS

| | | |
|---|---|---|
| 2006/0079933 A1 | 4/2006 | Hushka et al. |
| 2009/0088792 A1 | 4/2009 | Hoell, Jr. et al. |
| 2009/0171147 A1 | 7/2009 | Lee et al. |
| 2009/0312773 A1 | 12/2009 | Cabrera et al. |
| 2011/0230875 A1* | 9/2011 | Walberg ............ A61B 17/29 606/33 |
| 2012/0197190 A1 | 8/2012 | Suon et al. |
| 2013/0181034 A1* | 7/2013 | Shelton, IV ..... A61B 17/00234 227/176.1 |
| 2014/0263554 A1* | 9/2014 | Leimbach ............ A61B 34/76 227/176.1 |
| 2016/0100851 A1 | 4/2016 | Van Andel |
| 2016/0113732 A1 | 4/2016 | Steege et al. |
| 2016/0262738 A1 | 9/2016 | Altman |

FOREIGN PATENT DOCUMENTS

| | | |
|---|---|---|
| DE | 10 2008 048 615 A1 | 3/2010 |
| EP | 0 694 289 A1 | 1/1996 |
| EP | 2 316 366 A2 | 5/2011 |
| EP | 2636 380 A2 | 9/2013 |
| JP | 2015 198881 A | 11/2015 |
| WO | 9636289 A1 | 11/1996 |
| WO | 2010002904 A1 | 1/2010 |
| WO | 2016015233 A1 | 2/2016 |
| WO | 2016061291 A1 | 4/2016 |

OTHER PUBLICATIONS

Search Report, EP 18 152 176.6, dated May 24, 2018 (14 pgs.).
Search Report, DE 10 2017 101 093.9, dated Nov. 17, 2017 (11 pgs.).
Search Report, EP 18 152 176.6, dated Aug. 13, 2018 (17 pgs.).

* cited by examiner

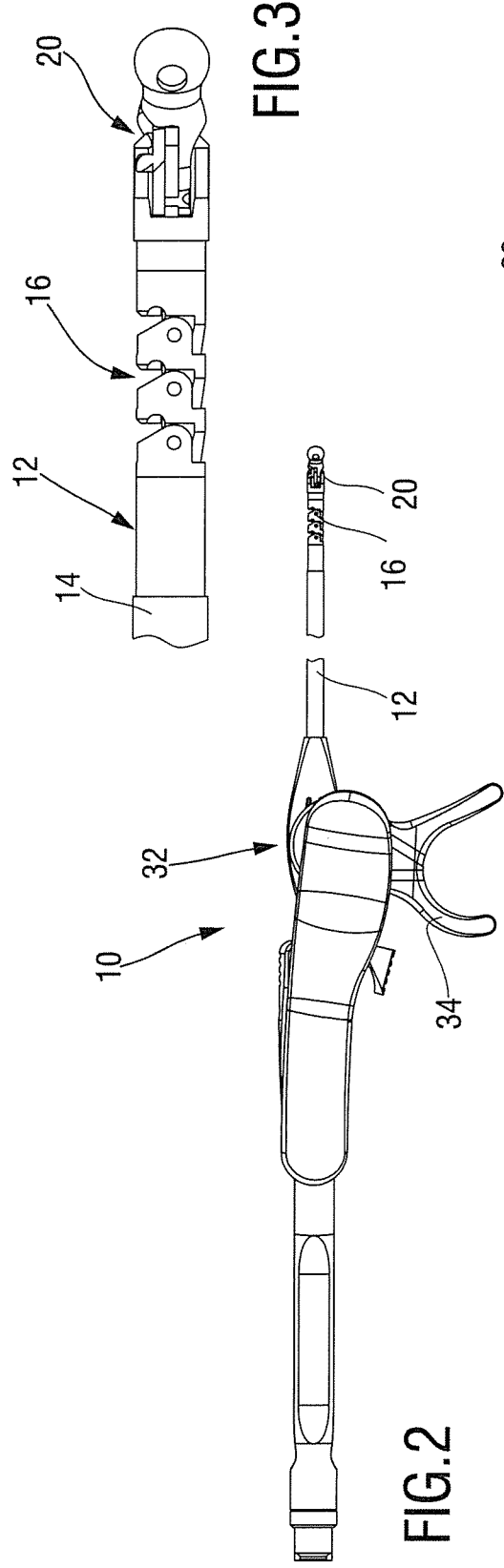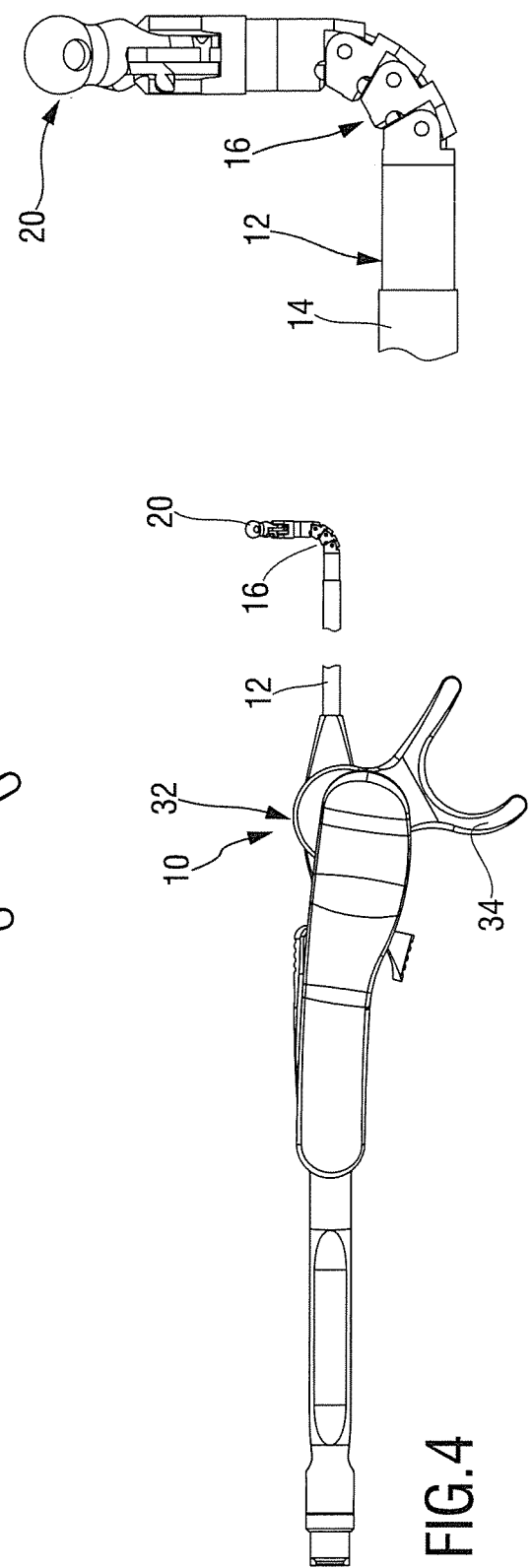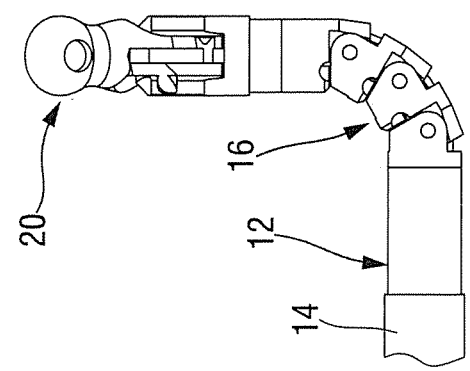

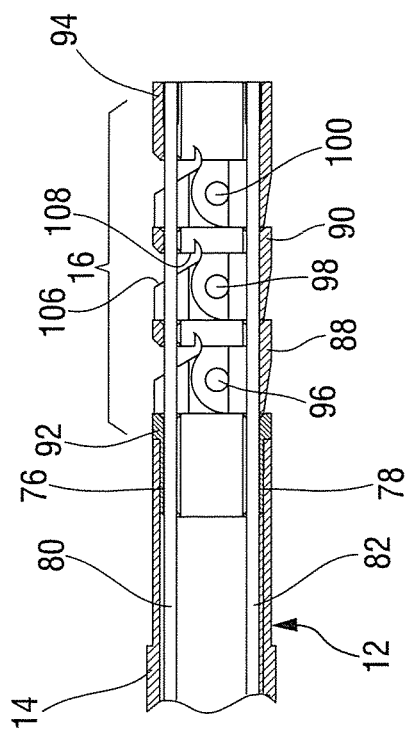
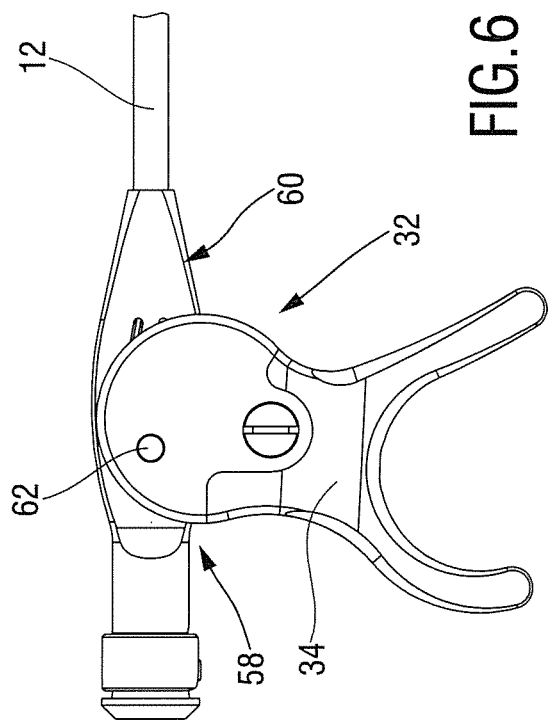
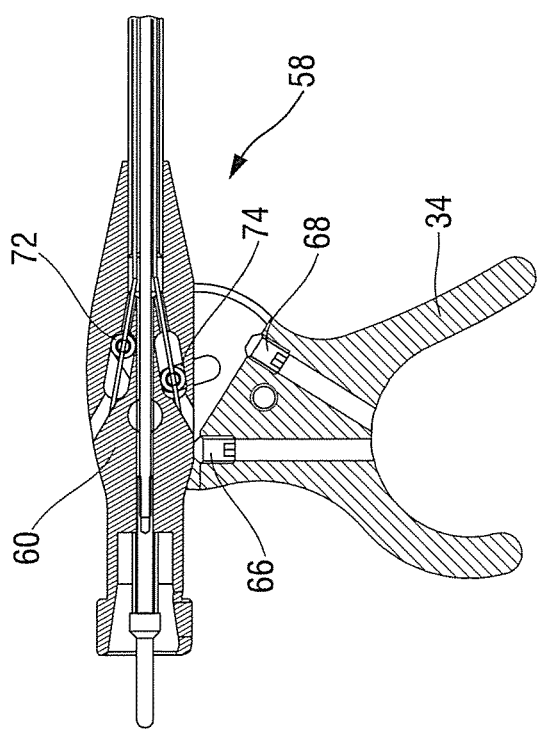

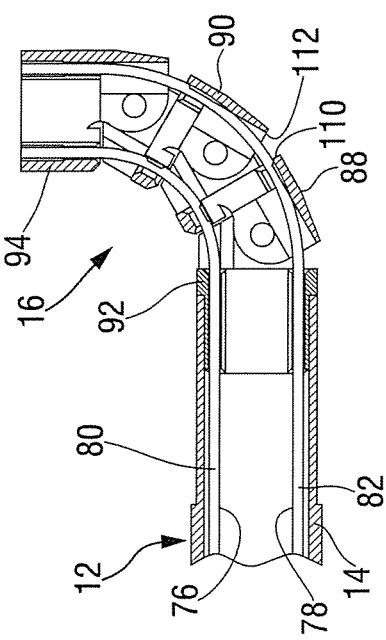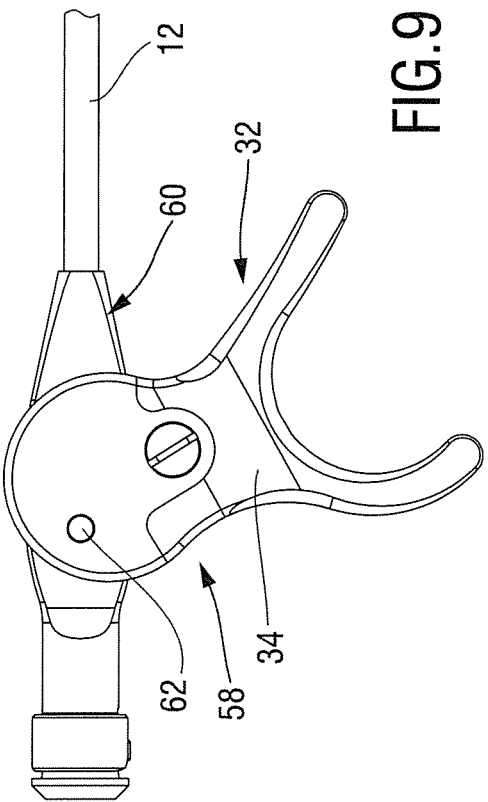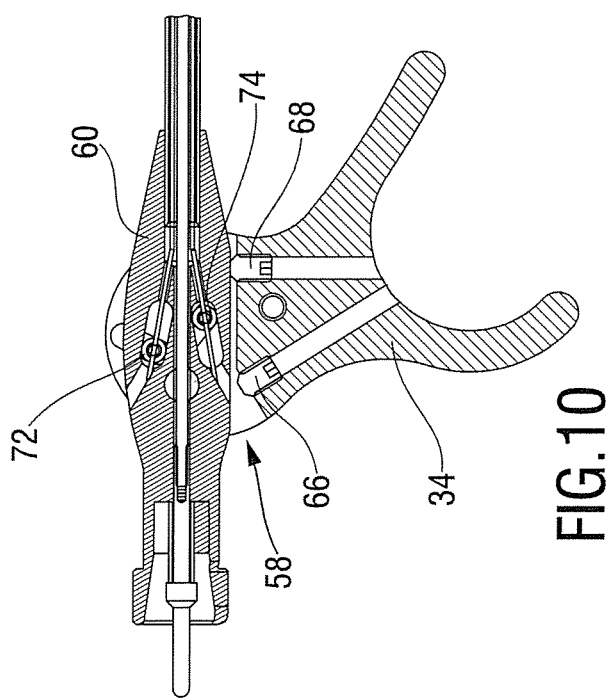

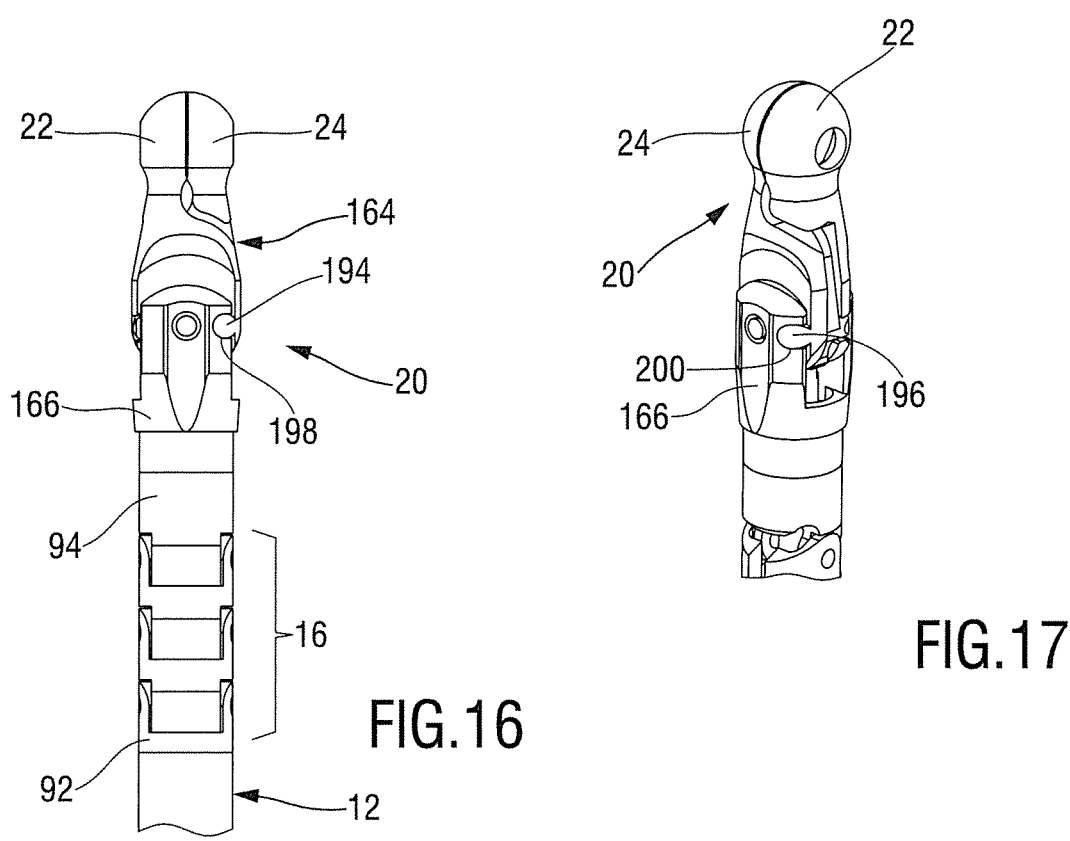
FIG.16
FIG.17
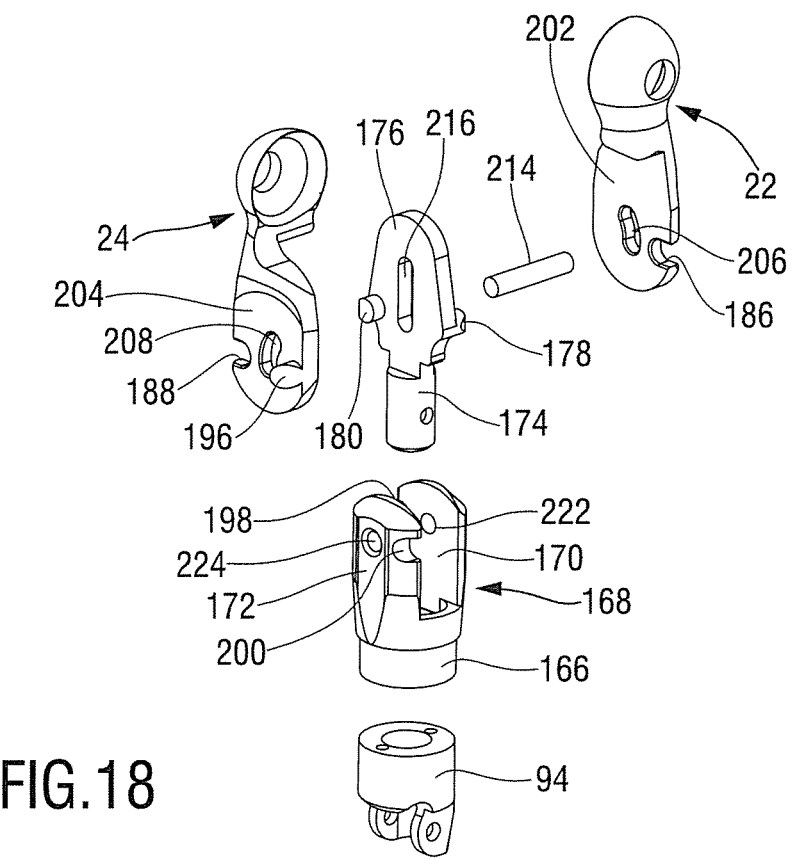
FIG.18

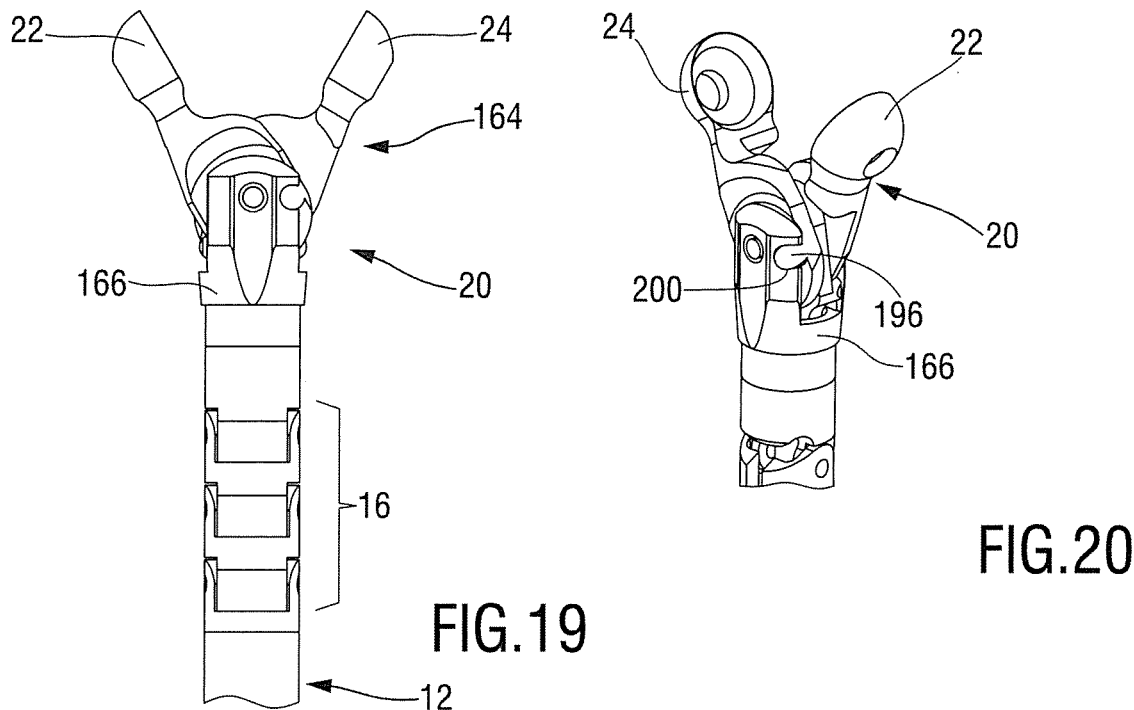
FIG.19
FIG.20
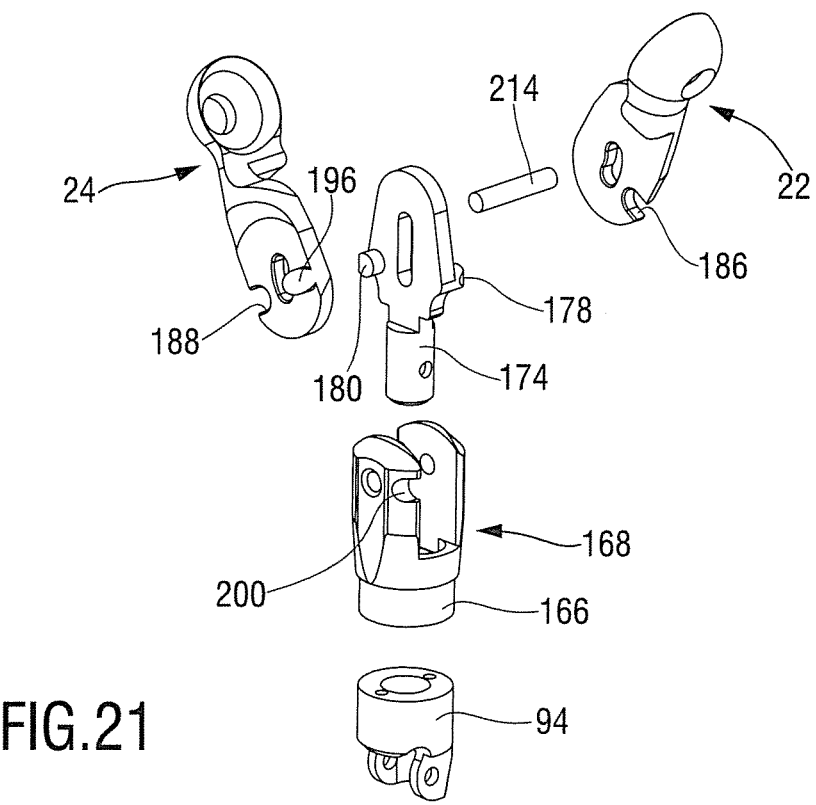
FIG.21

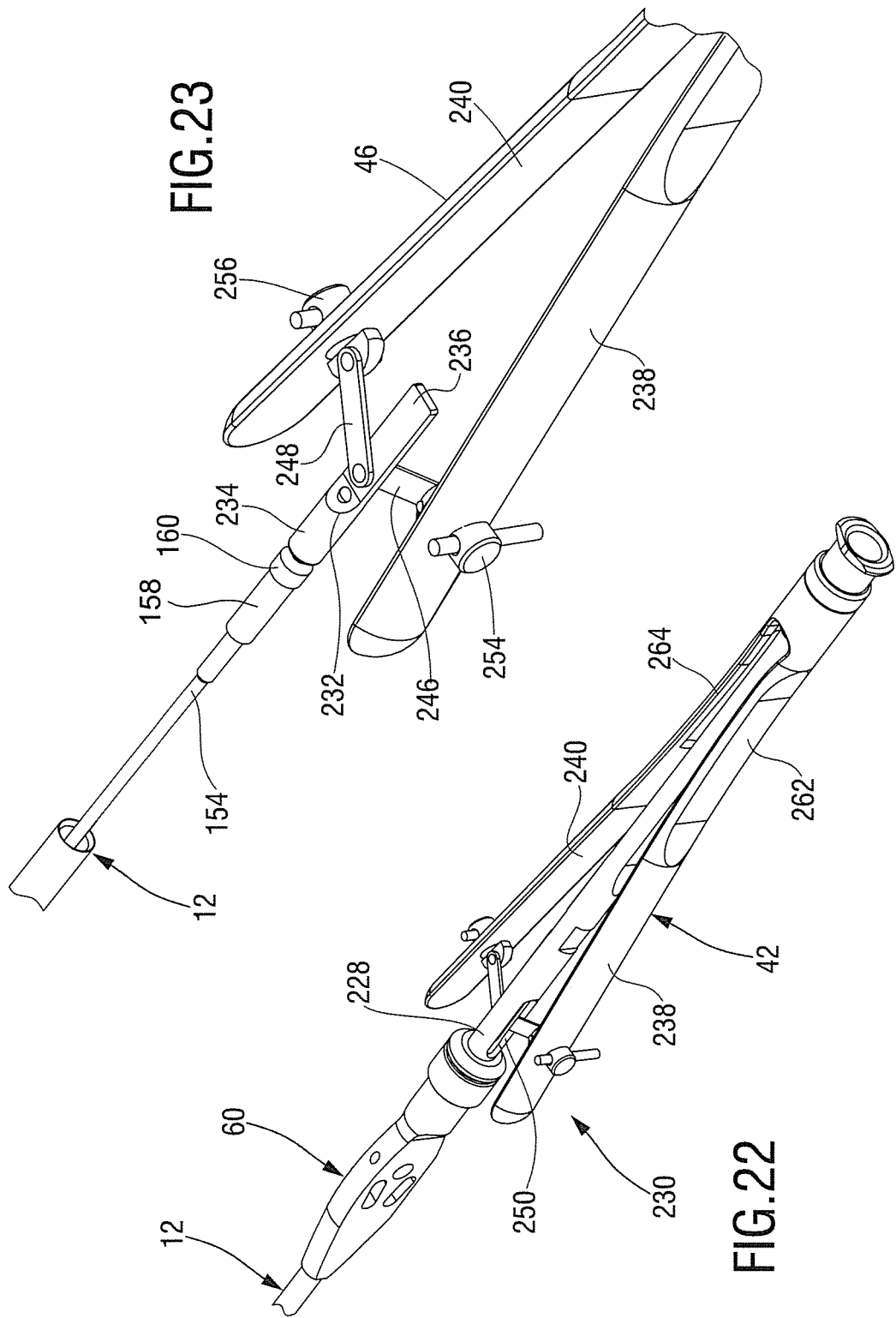

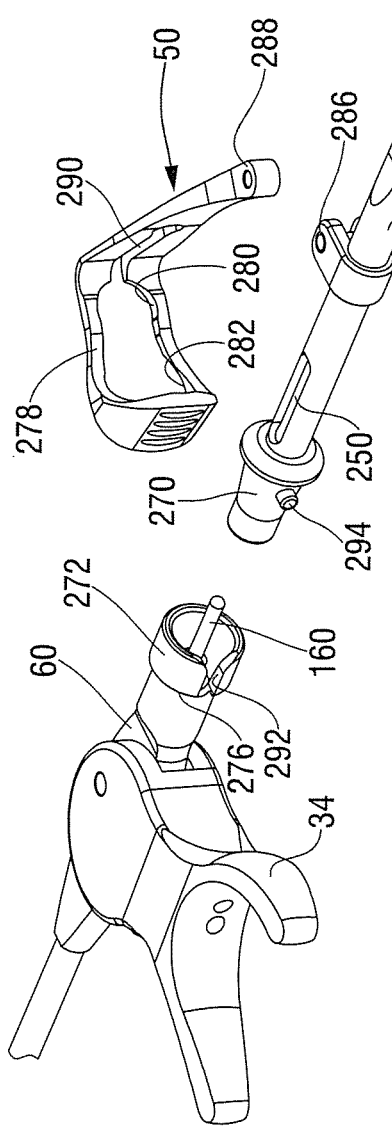
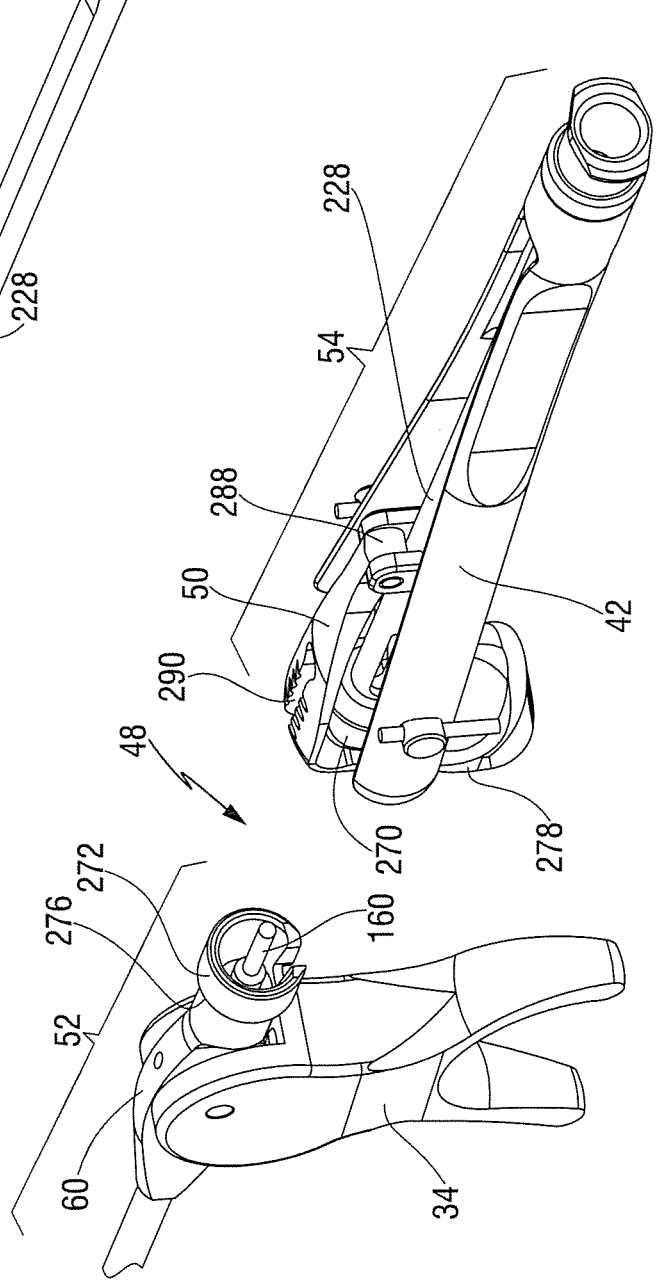

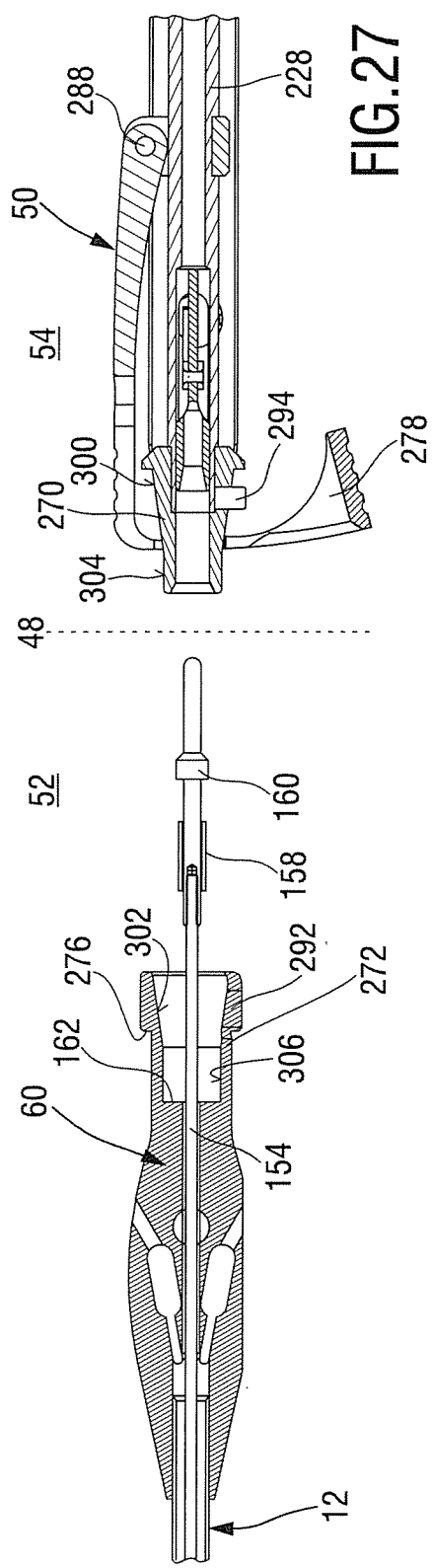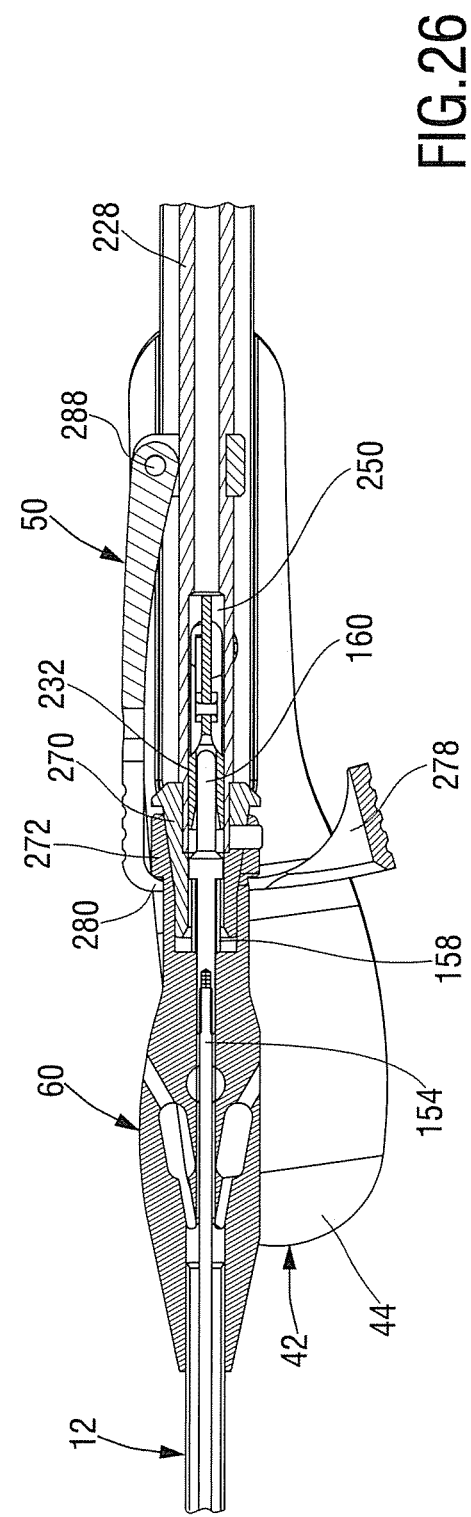

SURGICAL INSTRUMENT

CROSS-REFERENCES TO RELATED APPLICATIONS

This application claims priority from German patent application 10 2017 101 093.9, filed on Jan. 20, 2017. The entire content of that priority application is fully incorporated by reference herewith.

BACKGROUND

The present disclosure relates to a surgical instrument, for instance to an instrument that may be used for neurosurgery. Such an instrument may also be referred to as a neurosurgical instrument. Another field of application for such instruments is the field of brain surgery. The terms "brain surgery" and "neurosurgery" have an at least partially overlapping meaning.

Surgical Instruments in the context of the present disclosure include a shaft, a proximal handling portion at a proximal end of the shaft, and a distal effector at a distal end of the shaft, wherein the effector is controlled by an actuating mechanism. The effector may be a pair of pliers, scissors, a cutting edge, a clamp, a coagulation clamp and the like. It is also conceivable that the effector is arranged as a curette, biopsy forceps or similar.

In a general context, the present disclosure relates to instruments in the field of minimally invasive surgery. In this context, it should be noted that in the field of neurosurgery and/or brain surgery, very high requirements are in regard of the instrument's compactness, guiding accuracy, operability and precision in general are present. Generally, the above requirements also apply to standard surgical instruments, such as endoscopic and/or laparoscopic instruments. However, yet other criteria and requirements apply to neurosurgical instruments and/or brain surgical instruments. It has been observed that design principles which can be applied to surgical instruments and invasive instruments of a general nature are not directly transferable to neurosurgical and/or brain surgical instruments.

This does not preclude the use of instruments as defined in the present disclosure for ENT surgery (ear, nose and throat surgery) and other conventional fields of surgery. In general, such instruments can be used when little space consumption and certain flexibility are required. Instruments in accordance with the present disclosure may be arranged as miniature instruments, particularly in terms of their shaft diameter.

In the context of the present disclosure, a proximal side is a side of the instrument facing away from the patient and facing an operating surgeon. Accordingly, a distal side is a side of the instrument facing the patient and facing away from the operating surgeon. Particularly in the field of invasive surgery, the distal end of the instrument is inserted into the patient's body. Generally, the instrument is held or guided at the proximal end, whereas it is also conceivable to use arrangements in which the proximal end of the instrument extends beyond the handling portion.

From WO 96/36289 A1 there is known a small diameter neurosurgical instrument that is provided with a tube having a proximal end and a distal end; an axially displaceable flexible wire extending through said hollow tube, said wire having a proximal end and a distal end; a manual actuation means coupled to the proximal ends of said tube and said wire for axially displacing one of said tube and said wire relative to the other; a first end effector mechanically coupled to said distal end of said tube; and a second end effector mechanically coupled to said distal end of said wire and rotatably coupled to said first end effector, wherein a curved guiding channel is provided in either a proximal portion of said first end effector or a distal portion of said hollow conductive tube, and said axially displaceable conductive wire extending through said channel and is guided by said channel to move radially as well as axially when said manual actuation means axially displaces one of said tube and said wire relative to the other.

Neurosurgical or brain surgery treatment involves, for instance, the placement of an access point on a patient's skullcap. By way of example, a hole is drilled into the skullcap through which an instrument can be inserted into the skull. Conventional neurosurgical instruments, refer to the above WO 96/36289 A1, are provided with a straight shaft with an effector at its distal end, for instance in the form of pliers or a clamp. The shaft is not flexible and not deflectable.

The accesses to the patients inner body, for instance to the head and/or the spinal area, cannot be made arbitrarily large. The goal is to minimize trauma for the patient as much as possible. However, this setting can result in the instrument simply not being able to reach a desired target location inside the body, for instance in the patients head, because the shaft as a whole cannot be pivoted freely. This could possibly lead to the need of creating a further access.

In other fields of surgery, such as laparoscopic surgery, deflectable instruments are known. Such instruments have swivel mechanisms and/or deflection mechanisms that are formed, for instance, on the shaft itself or at the distal end of the shaft. In this way, an additional degree of freedom of movement can be provided for the instrument. By way of example, a pair of pliers mounted at the distal end of the instrument can be pivoted as a whole.

In this way, for instance, areas inside the body can be reached that are laterally spaced away from an imaginary main axis of the shaft. As already mentioned above, however, conventional endoscopic instruments and/or laparoscopic instruments are generally larger in size than neurosurgical instruments. By way of example, a shaft diameter of a laparoscopic instrument can be 10 mm, 12 mm, or even more. The shaft diameter of a neurosurgical instrument used in the field of brain surgery, for instance, is considerably smaller. In certain embodiments, a shaft diameter is less than about 3.5 mm. In certain embodiments, the shaft diameter is less than about 3.0 mm. In certain embodiments, the shaft diameter is less than about 2.7 mm or even less. For this reason alone, previously known design principles for deflectable and/or angled instruments cannot simply be transferred to the field of neurosurgery.

Another requirement that is specifically relevant for neurosurgical and/or brain surgical instruments is the accuracy of movement and/or positionability, positioning accuracy and positioning repeatability.

By way of example, in the case of surgical procedures performed in the patient's brain, minute deviations and inaccuracies can lead to damage to the adjacent tissue. Here, too, the design principles of well-known angled instruments from the field of laparoscopic surgery cannot simply be transferred to the field of neurosurgery.

Effective paths and movements of the instrument, e.g. in the patient's skull, are very small. This requires a distinct sensitivity and guidance accuracy of the instruments and the mechanisms incorporated therein. The ergonomics and manageability of neurosurgical instruments are very important.

The instrument should be positioned sensitively and with high precision. Positioning should be carried out with high repeat accuracy.

In general, it is conceivable to use neurosurgical instruments with nondeflectable/non-angled shafts. However, such instruments have only a very limited range of action. There are extreme cases where instruments with straight shafts simply cannot reach the area of application, because no suitable access (e.g. a hole in the skullcap) can be placed.

There is also a desire for dismountable instruments in the field of neurosurgery. A dismountable instrument comprises at least one interface at which modules of the instrument can be detached from each other in a defined way. This may apply to, for instance, a shaft assembly and a handle piece of the instrument. It has been observed that the design of dismountable instruments often leads to a reduction of accuracy. In other words, it can be observed that the corresponding interfaces required for the dismountability of the instruments often require an increase in mechanical play and hence a reduction of guidance accuracy.

Furthermore, surgical instruments that are designed to be bendable/deflectable often have interdependencies between the degrees of freedom involved. In other words, for instance, actuating an effector (e.g. opening and closing a forceps) can have a certain effect on a mechanism for the deflection/angle function of the instrument. This can also lead to a reduction of accuracy and an increase of the play in the system.

In view of this, it is an object of the present disclosure to present a surgical instrument, which can be operated with high accuracy and precision.

It is a further object of the present disclosure to present a surgical instrument that is suitable for neurosurgery and/or brain surgery, which can be operated with high accuracy and precision.

It is a further object of the present disclosure to present a surgical instrument providing degrees of freedom of movement that are controllable precisely and with high repeatability.

It is a further object of the present disclosure to present an instrument that is provided with only a small amount of play in the involved movement mechanisms for the degrees of freedom.

It is a further object of the present disclosure to present an instrument that is designed to be demountable, whereby the resulting interfaces do not adversely affect the accuracy and/or play in the system.

It is a further object of the present disclosure to present an instrument that enables an extended operating radius or an extended operating area, so that tissue areas can also be reached that are spaced from a main shaft axis when the instrument shaft is placed.

It is a further object of the present disclosure to present an instrument that enables a low backlash or even zero backlash control of both the effector and an angular position/deflection position of the effector as a whole with respect to the shaft.

SUMMARY

In accordance with a first aspect, these and other objects are achieved by a surgical instrument, comprising:
- a shaft, wherein an articulation section is formed at the shaft,
- a proximal handling portion at a proximal end of the shaft,
- a distal effector at a distal end of the shaft, and
- a deflection mechanism for controlling a bending state of the articulation section, comprising a first pull element, and a second pull element,
- wherein the first pull element and the second pull element are at least sectionally jointly pretensioned during the movement of the articulation section.

In certain embodiments, the instrument is arranged as an instrument for neurosurgery. The articulation section may be deflectable starting from a central position on one side of the shaft. In certain embodiments, the first pull element is used for a deflection movement, and the second pull element is used for a return movement.

In accordance with this exemplary aspect, the design of the pull elements namely allows a low backlash or even backlash-free deflection movement or deflection of the articulation section. This is achieved by the fact that both pull elements, of which originally only one is set under tension (tensile stress) when swiveling out and/or swiveling in, respectively, are put under tension together and in the same direction. This involves, for instance, that the deflection movement still takes place via a pull at the first pull element.

However, the second pull element is also pretensioned, at least sectionally, during the deflection movement, though only with considerably less tension than the first pull element. During the return movement the opposite applies, the second component is set accordingly under tensile stress. However, a tensile stress is applied to the first element at least sectionally, though only with a significantly lower stress level than that of the second pull element. The term "sectionally" refers here, for instance, to a certain pivot angle range during the adjustment movement.

In certain embodiments, the instrument is provided with an articulation section that can be deflected or folded away on one side. This has the effect that, for instance, a central position, where the articulation section is aligned with a longitudinal axis of the shaft, can simply be defined mechanically, for instance by means of suitable limit stops.

Overall, in certain embodiments, the deflection mechanism has low backlash or is has, in further embodiments, even zero backlash. This significantly increases the positioning accuracy and repeatability of the positioning of the instrument.

By way of example, surgical instruments suitable for neurosurgery and/or brain surgery have shaft diameters of less than 3.5 mm, less than 3.0 mm, or even equal to about 2.7 mm, or even less. Although this restriction of installation space limits the design freedom to a great extent, low backlash or zero backlash can be achieved by means of the pretensioning of the pull elements in the same direction.

In other words, for instance, a forced control or an overdetermined guide is provided for the first pull element and the second pull element. If this were not the case, the second pull element would be relieved during the deflection movement, for instance. The first pull element would be relieved during the return movement. The respective other element would be strained by tension. This would have the disadvantage that, for instance, if the direction of the adjustment movement of the articulation section is reversed, there would be a backlash in the deflection mechanism, which would lead to a reduced positioning accuracy and repeatability.

However, as both pull elements are pretensioned together in accordance with the above-mentioned aspect, such a reversal of movement can take place with little or no backlash. On the one hand, this can apply to extreme positions of the articulation section, such as a fully retracted position (middle position) and/or a fully extended position (fully deflected). At the same time, a reversing movement can also take place at an intermediate position between the extreme positions with little or no backlash, provided that both pull elements are preloaded in the same direction at the corresponding reversal point. A pretension in the same direction is present, for instance, if both pull elements are subjected to tensile stress.

In other words, the deflection mechanism for controlling the bending state is at least partially overdefined and/or overdetermined, in order to cause the desired state of pre-stressing of the pull elements. With a suitable design, this does not have to imply a detrimental effect on the actuating forces. Rather, the actuation is simplified because the low backlash or zero backlash design reacts immediately and directly to control movements.

In an exemplary embodiment of the instrument, the articulation section can be deflected on one side from a central position. According to this design, the articulation section cannot be deflected in the opposite direction from the central position.

In an exemplary embodiment of the instrument, the first pull element and the second pull element are simultaneously subjected to tensile stress when the articulation section is swiveled out or swiveled in. This has the effect that during a reversal of movement only little play or, in certain embodiments, no play at all can occur.

In an exemplary embodiment of the instrument, the first pull element is primarily provided for a deflecting movement and the second pull element is primarily provided for a return movement. Hence, during the deflection of the articulation section from the central position, the first pull element is actively pulled, whereas also the second pull element is slightly subjected to a pull force to maintain the desired little or no backlash design. Similarly, during the return movement of the articulation section into the central position, the second pull element is actively pulled, whereas also the first pull element is slightly subjected to a pull force to maintain the desired little or no backlash design.

In accordance with an exemplary embodiment of the instrument, the first pull element is formed as a first pull wire and the second pull element is formed as a second pull wire that are arranged on opposite sides of a center of the shaft. In this way, the pull elements can run eccentrically with respect to the longitudinal axis/middle axis of the shaft, at least sectionally. Hence, a force applied to one of the pull elements can cause a pivot movement of the articulation section in relation to the shaft, for instance with respect to a substantially rigid tube of the shaft.

In the embodiment described above, which comprises an articulated section that can be deflected from one side from a central position, the first pull wire can be referred to as an inner pull wire and the second pull wire can be referred to as an outer pull wire, where the terms "inside" and "outside" relate to the resulting radius of curvature during the deflection. By way of example, the pull elements are arranged in a common plane, which also intersects with the longitudinal axis of the shaft. In this plane, the pull elements are located on opposite sides of the longitudinal axis. The pull elements are connected to an effector mount for the effector at the distal end of the shaft. A pull force applied to one of the two pull elements in a proximal direction causes the deflection movement or the return movement, whereas at least a slight tensile stress is present at the other pull element. This may significantly reduce or even eliminate play in the deflection mechanism.

In accordance with an exemplary embodiment of the instrument, the pull elements each extend between a proximal coupling point and a distal coupling point in the shaft, respectively, and wherein the pull elements are coupled at their proximal end with a control unit that comprises a pivotable control lever. Accordingly, the control lever can be pivoted, for instance, about a pivot axis that is perpendicular to the longitudinal axis of the shaft.

In accordance with an exemplary embodiment of the instrument, the control unit provides a forced control for the first pull element and the second pull element. This can be achieved, for instance, by appropriately designing the pivotable control lever. The control lever can be arranged as part of a flat cam gear. A deliberate overdetermined and/or overdefined design of the cam gear causes a slight pretensioning of the pull element, which is not actually necessary for the respective movement as such (swiveling in/out).

The coupling points of the pull elements can also be arranged in a plane that intersects with the longitudinal axis defined along the shaft. The pull elements can be arranged parallel along the shaft, at least sectionally.

The control unit with the pivotable control lever is significantly separated from the distal end of the shaft. The control unit may be provided at the proximal end of the shaft. This has the effect that at the distal end itself, where the effector is mounted, no specific arrangement is required in order to generate the desired tensile stress in the other pull element, which is necessary for the low backlash or zero backlash.

In accordance with an exemplary embodiment of the instrument, the control unit comprises at the control lever a first guideway for the first pull element and a second guideway for the second pull element, wherein at the handling portion a first guideway for the first pull element and a second guideway for the second pull element is provided, wherein the first guideway and the second guideway at the handling portion are, in specific embodiments, inclined with respect to a longitudinal axis of the shaft, wherein the first pull element is coupled with the first guideway at the handling portion and the first guideway of the control lever, and wherein the second pull element is coupled with the second guideway at the handling portion and the second guideway of the control lever.

The control lever, for instance, is pivotable on a bearing block that is coupled to the shaft. Accordingly, the first guideway and the second guideway of the handling section can be formed on the bearing block.

By way of example, the first pull element and the second pull element at their respective proximal ends are each coupled with a slider, for instance in the form of a pin. The slide piece for the first pull element is accommodated both in the first guideway on the control lever and in the first guideway on the bearing block. The second slide piece is accommodated in the second guideway on the control lever as well as in the second guideway on the bearing block. The respective first and second guideways on the control lever are offset (angular and radial) to a pivoting axis of the control lever such that, when the control lever is actuated, the slide pieces are caused by the guideways of the control lever to be moved, i.e. to be displaced in the guideways formed on the bearing block. The first and second guideways of the control unit are formed in such a way that a length offset resulting from the adjustment movement of the articulated section of the pull elements is compensated.

As already elucidated above, the first pull element may be referred to as an internal pull element and the second pull element as an external pull element If the articulation section is pivoted by a certain angle, the resulting path for the inner pull element is considerably smaller than for the outer pull element.

In accordance with a further exemplary embodiment of the instrument, the guideways for the first pull element and the second pull element are arranged for compensating a length offset that is caused by different bending radii of the first pull element and the second pull element during the deflection and return of the deflection mechanism.

In this way, it is taken into account that the second tensioning element, for instance, travels a greater distance than the first tensioning element when the control lever is pivoted and the pivot movement of the articulation section results therefrom.

In specific embodiments, however, compensation of the length offset does not include full compensation. By way of example, the guideways are designed in such a way that at least a minimum length offset and/or displacement remains when the control lever is pivoted. In this way, the desired preload can be generated. The control unit can be designed with little or no play.

In accordance with a further exemplary embodiment of the instrument, the guideways are arranged such that when alternating between two bending states both pull elements are at least sectionally subjected to tension. In specific embodiments, the pull elements are subjected to tensile stress, at least when alternating between the two bending states.

It is conceivable to permanently pretension both pull elements slightly, i.e. to apply tensile stress along their longitudinal extension. This pretensioning can be provided in any position of the articulation section. It goes without saying that a slight pretension is sufficient to minimize or even eliminate the play. The deflection mechanism can be designed with friction so that self-locking is achieved if no actuating or adjusting forces are applied. In this way, a current deflection position can be maintained securely, even if both pull elements are pre-stressed.

In accordance with a further exemplary design of the instrument, the pull elements consist of a superelastic alloy. By way of example, the pull elements can be made of nitinol, such as nitinol wires. Superelastic materials and alloys exhibit a so-called pseudoelastic or superelastic behavior. In general, shape memory alloys, including nitinol, exhibit such behavior. Similar to ideal spring steel, such materials are very malleable, whereby virtually no plastic deformation occurs. In other words, such materials can retain their original shape even with frequent load changes and load cycles.

In accordance with a further exemplary design of the instrument, the articulation section comprises a plurality of articulated links that are articulatedly connected in a series with each other, wherein the articulated links are provided with limit stops for defining at least one bending state without play and wherein the limit stops of adjacent articulated links contact each other in a first state of the shaft and are spaced away from one another in a second state.

In other words, this means that for at least one of the two extreme positions that the effector can assume in relation to the shaft, a highly accurate and accurately repeatable positioning is possible. This is ensured by the limit stops that contact each other in the respective position and prevent further movement.

By way of example, the articulation section as a whole can be swiveled out sidewards from a central position in which it is aligned with the longitudinal axis of the shaft, wherein the sideward swiveling comprises a relative swiveling between the articulated links of the articulation section. Accordingly, the articulated links can be provided with stops which are in a spaced-apart state linearly and/or angularly apart from each other.

According to an exemplary embodiment of the instrument, the first state is a straight, undeflected state in which the shaft is in the central position, and wherein the second state is a deflected state. In accordance with an exemplary embodiment, the articulated links are provided with further limit stops, wherein limit stops of adjacent articulated links contact one another in the second state of the shaft, and are spaced apart from one another in the first state of the shaft.

The extreme positions (first and second state) may comprise a 0° position and a 90° position in relation to a longitudinal axis of the shaft. Each of the two extreme positions can be associated with a limit stop formed by individual limit stops of the articulated joints.

In accordance with a further exemplary embodiment of the instrument, at least one elastic clamping body for increasing friction is provided, for instance at least one elastomer ring, that causes the actual bending state of the shaft to be in a secured position. In accordance with this embodiment, deliberate measures are taken at the deflection mechanism to increase friction. In specific embodiments, friction can be increased to such an extent that self-locking occurs as long as the handling force at the control lever does not exceed a certain level. In specific embodiments, when no handling force is applied to the control lever, the friction in the deflection mechanism may reach a level that fixes the current bending state of the articulation section. It should be noted in this context that, at least according to some exemplary embodiments, there is an inherent pretensioning in the pull elements. In specific embodiments, friction in the deflection mechanism is increased to such an extent that these base forces minimize or eliminate play in the system, but do not cause self-adjustment of the articulation section.

By way of example, the elastic clamping body can be provided on the control lever. This may include, for instance, in an exemplary embodiment at least one O-ring made of elastic material that surrounds the pivot axis and that is accommodated under preloading between the control lever and a housing/bearing part of the handling section. This has the effect that the position securing takes place again at the proximal handling portion and not at the distal end of the shaft. Generally, it is also conceivable to provide such clamping bodies, for instance, at the articulation section. However, this would in turn increase the manufacturing efforts and assembly efforts in the area of the very small distal end of the shaft.

In accordance with a further aspect of the present disclosure, these and other objects are achieved by a surgical instrument, comprising:
  a shaft,
  a proximal handling portion at a proximal end of the shaft,
  a distal effector at a distal end of the shaft, and
  an interface where the instrument is demountable into a distal and a proximal part.

In certain embodiments, the instrument is arranged as an instrument for neurosurgery. In certain embodiments, at the shaft an articulation section is formed. In certain embodiments, the articulation section is deflectable on one side, starting from a central position. In certain embodiments, the instrument is demountable into a distal shaft assembly and a proximal handle piece.

In accordance with this exemplary aspect, the interface namely allows a simple separation and/or disassembly of the Instrument. This may, by way of example, considerably simplify the manufacture, assembly, handling, maintenance, repair and/or cleaning of the instrument.

An exemplary embodiment in accordance with the above-mentioned aspect may generally be combined with arrangements according to other aspects described herein. Nevertheless, this aspect alone also forms a disclosure that can be the subject of independent claims. Accordingly, the subject matter in accordance with the foregoing aspect may be pursued in the context of this application and/or in the context of divisional applications, in isolation and/or in any combination with arrangements according to the other aspects.

The terms "shaft assembly" and "handle piece" should not be understood in a limiting way. By way of example, the term "handle piece" does not exclude the possibility that handle elements, actuating elements or the like are also formed at the shaft assembly. Generally speaking, the term "shaft assembly" refers to a distal part of the instrument. Generally speaking, the term "handle piece" refers to a proximal part of the instrument. By way of example, it is conceivable to associate the deflection mechanism for the articulation section with the shaft assembly. Furthermore, it is conceivable to arrange an actuation mechanism for the effector at least partially on the handle piece.

In specific embodiments, the design of the interface allows low backlash or even backlash-free coupling. For instance, the design of the interface allows a rattle-free coupling of the shaft assembly and the handle piece, in specific embodiments.

In accordance with a further exemplary embodiment of the instrument, the interface comprises mating parts that comprise a male part and a female part that can be coupled with one another. For guiding purposes, in specific embodiments, cylindrical surfaces are provided, which ensure concentric alignment.

The mating parts may also be provided with conical surfaces, wherein further, in specific embodiments, cylindrical surfaces are also formed on the mating parts for guiding purposes. In this way, both concentric alignment and axial alignment between the shaft assembly and the handle can be achieved via the mating parts. The cylindrical surfaces can transfer guide forces and thus reduce the load on the conical surfaces when using the instrument. In specific embodiments, the cylindrical surfaces are adjoining the conical surfaces, so that for instance the conical surface of the female part serves as a mounting aid for the cylindrical surface of the male part.

The male part may also be referred to as inner part. The female part may also be referred to as outer part. At least one of the two parts is directly or indirectly coupled to the shaft when the instrument is dismantled at the interface. Accordingly, the other part of the two parts is directly or indirectly connected to the handle, when the instrument is dismantled.

In accordance with a further exemplary embodiment of the instrument, with the interface there is associated a locking bracket that is arranged to engage a retaining portion to secure an axial relative position between the shaft assembly and the handle piece. By way of example, the locking bracket is articulatedly arranged at the handle piece. By way of example, the retaining portion is arranged at the shaft assembly and, in specific embodiments, formed at a bearing part of the shaft assembly.

The locking bracket is designed to overlap the retaining portion. The retaining portion is designed as a shoulder, for instance. By way of example, the locking bracket may be articulatedly mounted on a support shaft that is disposed at the handle piece. Hence, the locking bracket may also be pivoted relative to a longitudinal axis of the instrument. A pivoting axis of the locking bracket is therefore perpendicular to the longitudinal axis of the instrument, at least in exemplary embodiments.

In accordance with another exemplary embodiment of the instrument, the locking bow is arranged to be flexible. The locking bracket comprises a sufficiently elastic design and is, accordingly, for instance, made of metal material, e.g. stainless steel. There may be provided a locking bracket based on stainless steel sheet metal. Alternatively, the locking bracket is made of plastic. The locking bracket may provide a low backlash or zero backlash position lock for the assembled state of the instrument. The locking bracket locks the interface, preferably with little or no backlash, for instance in an axial direction along the longitudinal extension of the instrument. In this way, the locking bracket secures the position definition caused by the design of the mating parts.

In accordance with a further exemplary embodiment of the instrument, at the locking bracket a retaining arm is formed that at least sectionally encompasses the retaining portion. By way of example, the retaining arm Includes a position securing section and a widened release section. Accordingly, the design of the locking bracket makes it easier to open and lock the interface. Operator ergonomics is also improved. The risk of operating errors can be reduced.

By way of example, the retaining arm is arranged at a distal end of the locking bracket. The locking bracket is, for instance, mounted on the support shaft and extends towards the retaining portion, which is provided on the bearing part, for instance. By pivoting the locking bracket, the retaining arm can be brought into engagement with the support section or disengaged from the support section.

In other words, the locking bracket itself is the "tool" to lock or open the interface. The interface therefore allows the instrument to be connected and disconnected without the need of tools.

According to an exemplary embodiment, the retaining arm extends essentially perpendicular to the longitudinal axis of the instrument. The retaining portion and the release section can together define a keyhole contour, with the retaining portion forming the bottleneck and the release section forming the widened spot.

In accordance with a further exemplary embodiment of the instrument, the locking bracket is pretensioned towards a locking position and releasable by an opposite movement. This ensures that the interface is not accidentally unlocked.

In accordance with a further exemplary embodiment of the instrument, the interface also comprises a rotary position lock. By way of example, the rotary position lock may include a guide pin which engages an axially extending groove that is open at least on one end. By way of example, the guide pin is mounted on the male mating part. Accordingly, the groove is formed on the female mating part. The guide pin may be oriented radially in relation to the longitudinal axis of the instrument.

In accordance with a further exemplary embodiment of the instrument, the interface further comprises a releasable coupling between a pressure piece at the proximal end of a push piece for controlling the effector and a slider for applying force to the pressure piece. In this way, the interface may also extend over at least one mechanism of the instrument and, in specific embodiments, comprise easily releasable joining parts. In this context, it is conceivable to control the effector by means of a push piece, i.e. by means of an element that can be subjected to push force. Accordingly, the slider that may be coupled to the pressure piece may namely be pushed on in a simple way during assembly of the shaft assembly and the handle piece, and removed during disassembly. The pressure piece may also be referred to as plunger or tappet.

In accordance with a further aspect of the present disclosure, these and other objects are achieved by a surgical instrument, comprising:
  a shaft,
  a proximal handling portion at a proximal end of the shaft, and
  a distal effector at a distal end of the shaft,
  wherein the effector is controlled via an actuation mechanism that comprises a push piece.

In certain embodiments, the instrument is arranged as an instrument for neurosurgery. In certain embodiments, at the shaft an articulation section is formed. In certain embodiments, the articulation section is deflectable on one side, starting from a central position. In certain embodiments, the push piece is arranged as one a push rod and a push wire.

In accordance with the present disclosure, the actuation of the effector via a push piece (and not a via pull bar or pull wire) allows the effector to be actuated with no effect or only little effect on a current pivot state of the shaft, for instance on a current pivot state of an articulation section. This may contribute to a further minimization of the play in the instrument's various degrees of freedom. Furthermore, possible feedback between the effector's degree of freedom and the deflection mechanism's degree of freedom can be minimized or even completely avoided.

An exemplary embodiment in accordance with the above-described aspect may generally be combined with arrangements according to other aspects described herein. Nevertheless, this aspect alone also forms a disclosure that can be the subject of independent claims. Accordingly, the subject matter in accordance with the foregoing aspect may be pursued in the context of this application and/or in the context of divisional applications, in isolation and/or in any combination with arrangements according to the other aspects.

In accordance with an exemplary embodiment of the instrument, the effector comprises a first jaw part and a jaw part that are pivotable with respect to one another. This involves designs in which both jaw parts can be pivoted towards and away from each other. Furthermore, however, embodiments are also conceivable in which only one jaw part can be pivoted in relation to the other jaw part. By way of example, the jaw parts can be pivoted between a first, closed position and a second open position.

The term "pivoting" and/or "pivoting movement" should not be understood to be limiting. Generally, this is to be understood to mean that the jaw parts are moved towards each other and moved away from each other in order to move them between the first and the second position.

The effector design can be envisaged, for instance, as a gripper, tongs, scissors, a clamp and the like. An arrangement as a coagulation clamp is also conceivable. Furthermore, the design of the effector as curette, biopsy forceps or similar is conceivable.

According to an exemplary embodiment, the effector can be moved from the second, open position to the first, closed position by pressing the push piece towards the distal end of the shaft. Hence, in accordance with a further exemplary embodiment of the instrument, the push piece is moved distally in order to move the first jaw part and the second jaw part towards each other, for instance to close them.

In accordance with a further exemplary embodiment of the instrument, wherein the push piece is connected at its distal end with a coupling piece that comprises a first driver for the first jaw part and a second driver for the second jaw part, wherein the first jaw part comprises a driving recess, wherein the second jaw part comprises a driving recess, wherein the first driver of the coupling piece engages the driving recess of the first jaw part, and wherein the second driver of the coupling piece engages the driving recess of the second jaw part.

This may involve exemplary embodiments wherein the drivers of the coupling piece are arranged on opposite sides of the coupling piece, wherein the drivers are also spaced away from one another in a direction perpendicular to a pivoting direction of the effector and perpendicular to an actuation direction of the push piece.

In accordance with a further exemplary embodiment, the instrument further comprises a head piece at the distal end of the shaft, wherein the first jaw part is pivotably mounted at the head piece, wherein the second jaw part is pivotably mounted at the head piece, and wherein pivot axes of the first jaw part and the second jaw part are parallel to and spaced away from one another.

This may involve exemplary embodiments, wherein the head piece is arranged at the distal end of the articulation section. In certain embodiments, the headpiece is arranged as a clevis head and includes a first side piece and a second side piece, between which the coupling piece as well as the first jaw and the second jaw are accommodated. In specific embodiments, the coupling piece is located centrally between the first jaw part and the second jaw part. By way of example, the pivot axes of the first jaw part and the second jaw parts are respectively defined by a projection and a corresponding bearing recess.

In accordance with a further exemplary embodiment of the instrument, the first jaw part comprises a guideway, wherein the second jaw part comprises a guideway, and wherein a guide pin that is arranged at the head piece is accommodated in the guideway of the first jaw part and the guideway of the second jaw part. In this way, it is possible to provide a forced control also for the effector, which reduces or even eliminates the play in the mechanism. In turn, the guideways can be designed in such a way that a forced control is provided for the guide pin.

By way of example, the guide pin is formed parallel to the pivot axes of the two jaw parts. The guide pin may be arranged in a plane between the pivot axes of the two jaw parts.

In accordance with a further exemplary embodiment of the instrument, the coupling piece extends at least sectionally between the first jaw part and the second jaw part, and wherein the guide pin extends through a recess of the coupling piece. Accordingly, an additional position lock is ensured.

By way of example, the coupling piece may comprise in the portion in which it extends between the first jaw part and the second jaw part a flat tongue with a longitudinal groove for the guide pin.

In accordance with a further exemplary embodiment of the instrument, at the proximal end of the push piece a pressure piece is provided that can be coupled with a slider, wherein the slider is mounted at the handling portion in a longitudinally displaceable manner, and wherein the slider is coupled with a handle that comprises at least one actuating section that is pivotably accommodated at the handling portion. In this way, both the actuation mechanism at the proximal end of the push piece and the control mechanism at the distal end of the push piece are respectively arranged as coupling mechanisms. In this way, the guiding accuracy can be increased. The handle may be arranged in the form of pliers, wherein, in specific embodiments, two actuation sections are provided, which enclose a support shaft of the handle therebetween. Accordingly, the handling sections can be pushed towards one another to move the slider distally to close the effector.

In accordance with a further exemplary embodiment of the instrument, at the handling portion a coupling mechanism is formed that comprises the handle, the slider and at least one coupling member, wherein a pivoting movement of the at least one actuating section is converted into a pushing movement of the slider.

By way of example, the coupling mechanism is arranged in the form of a slider rocker mechanism. Provided that the handle comprises two actuating sections, the coupling mechanism may be arranged in the form of a double slider rocker. This may in turn increase the sensitivity and definiteness of the effector's operation. The coupling mechanism for actuating the pressure piece forms a part of the actuation mechanism for the effector.

In accordance with a further exemplary embodiment of the instrument, the handle is arranged in a pincer-like manner and provided with two arms that are associated with the actuating sections, and that are opened towards the proximal end of the shaft, and wherein the arms at least sectionally laterally encompass the locking bracket and the control lever.

In this way, the instrument as a whole may comprise a compact shape and advantageous ergonomics. The arms of the handle cover at least a substantial portion of the support laterally. A further effect of the above exemplary embodiment is the beneficial field of view for the operating surgeon handling the instrument. This may further simplify control and actuation.

In accordance with a further exemplary embodiment of the instrument, along a main extension direction of the instrument, seen from proximal to distal, the handle, the locking bracket and the control lever are successively articulatedly arranged, wherein pivot axes of the locking bracket and the control lever are parallel to one another, wherein a pivoting movement of the handle takes place about a pivot axis that is perpendicular to the pivot axes of the locking bracket and the control levers, and wherein, in specific embodiments, the handle and the locking bracket are articulatedly arranged at a support shaft of the handle piece. In accordance with exemplary embodiments, the pivot axes of the handle, the locking bracket and the control lever are all perpendicular to the longitudinal axis of the instrument.

By way of example, at least the handle can be arranged in such a way that no distinctively defined pivot axis is provided. Instead, by way of example, the handle may be elastically deformable and is provided with a living hinge, for instance. This results in an imaginary pivot axis for the handle.

In accordance with a further exemplary embodiment of the instrument, the push piece is proximally pretensioned at a proximal end by a spring, wherein the spring extends between the pressure piece and a distal limit stop at the handling portion. In this way, also the push piece may be permanently subjected to a certain pretensioning. This may further reduce the play in the actuation mechanism for the effector, for instance the play when reversing the movement.

At least some of the aspects and exemplary embodiments of surgical instruments described above allow for an improved function and provide a plurality of degrees of freedom, all of which are designed with little play or backlash-free. Nevertheless, the instruments may still be miniaturized. The weight of the instruments may be very low. In certain embodiments, this results in a beneficial center of gravity at the instrument for the operating surgeon. In addition, in certain embodiments, a beneficial field of view results therefrom as the instrument is very compact and integrally shaped.

It is to be understood that the previously mentioned features and the features mentioned in the following may not only be used in a certain combination, but also in other combinations or as isolated features without leaving the spirit and scope of the present disclosure.

BRIEF DESCRIPTION OF THE DRAWINGS

Further features and advantages of the disclosure are disclosed by the following description of a plurality of exemplary embodiments, with reference to the drawings, wherein:

FIG. 2 is a broken side view of the instrument according to FIG. 1, in a first pivoting state;

FIG. 3 is an enlarged view of the distal end of the instrument as shown in FIG. 2;

FIG. 4 is a broken side view of the instrument according to FIG. 1 in a second pivoting state deviating from the state according to FIG. 2

FIG. 5 is an enlarged view of the distal end of the instrument according to FIG. 4;

FIG. 6 is a partial side view of a deflection mechanism of a neurosurgical instrument;

FIG. 7 is a cross-sectional view of the arrangement as shown in FIG. 6;

FIG. 8 is a cross-sectional enlarged view of an articulation section at the shaft of an instrument, the deflection state of the articulation section corresponding to the state of the deflection mechanism shown in FIGS. 6 and 7;

FIG. 9 is an arrangement according to FIG. 6 in a second pivoting state;

FIG. 10 is an arrangement according to FIG. 7 in a second pivoting state;

FIG. 11 is an arrangement according to FIG. 8 in a second pivoting state;

FIG. 16 is a side view of a distal end of a neurosurgical instrument that is provided with a closed effector;

FIG. 17 is a perspective view of the arrangement according to FIG. 16;

FIG. 18 is an exploded representation of the arrangement according to FIGS. 16 and 17 in an orientation according to that shown in FIG. 17;

FIG. 19 is an illustration of the arrangement according to FIG. 16 in an open state of the effector;

FIG. 20 is a further illustration of the arrangement according to FIG. 17 in an open state of the effector;

FIG. 21 is a further illustration of the arrangement according to FIG. 18 in an open state of the effector;

FIG. 22 is a rear perspective view of a coupling mechanism for a neurosurgical instrument, for controlling an effector;

FIG. 23 is an enlarged arrangement of the coupling mechanism according to FIG. 22, with further components omitted for illustrative purposes;

FIG. 24 is a perspective rear view of an interface for a neurosurgical instrument;

FIG. 25 is a further rear perspective view of an interface for a neurosurgical instrument, in an orientation different from that shown in FIG. 24, with a locking bracket shown in FIG. 25 isolated for illustrative purposes;

FIG. 26 is an enlarged cross-sectional view of a neurosurgical instrument joined at an interface; and FIG. 27 is a further cross-sectional side view of an instrument, for instance as shown in FIG. 26, whereas in FIG. 27 a shaft assembly and a handle of the instrument are detached from each other.

DETAILED DESCRIPTION OF EXEMPLARY EMBODIMENTS

Figure 1:
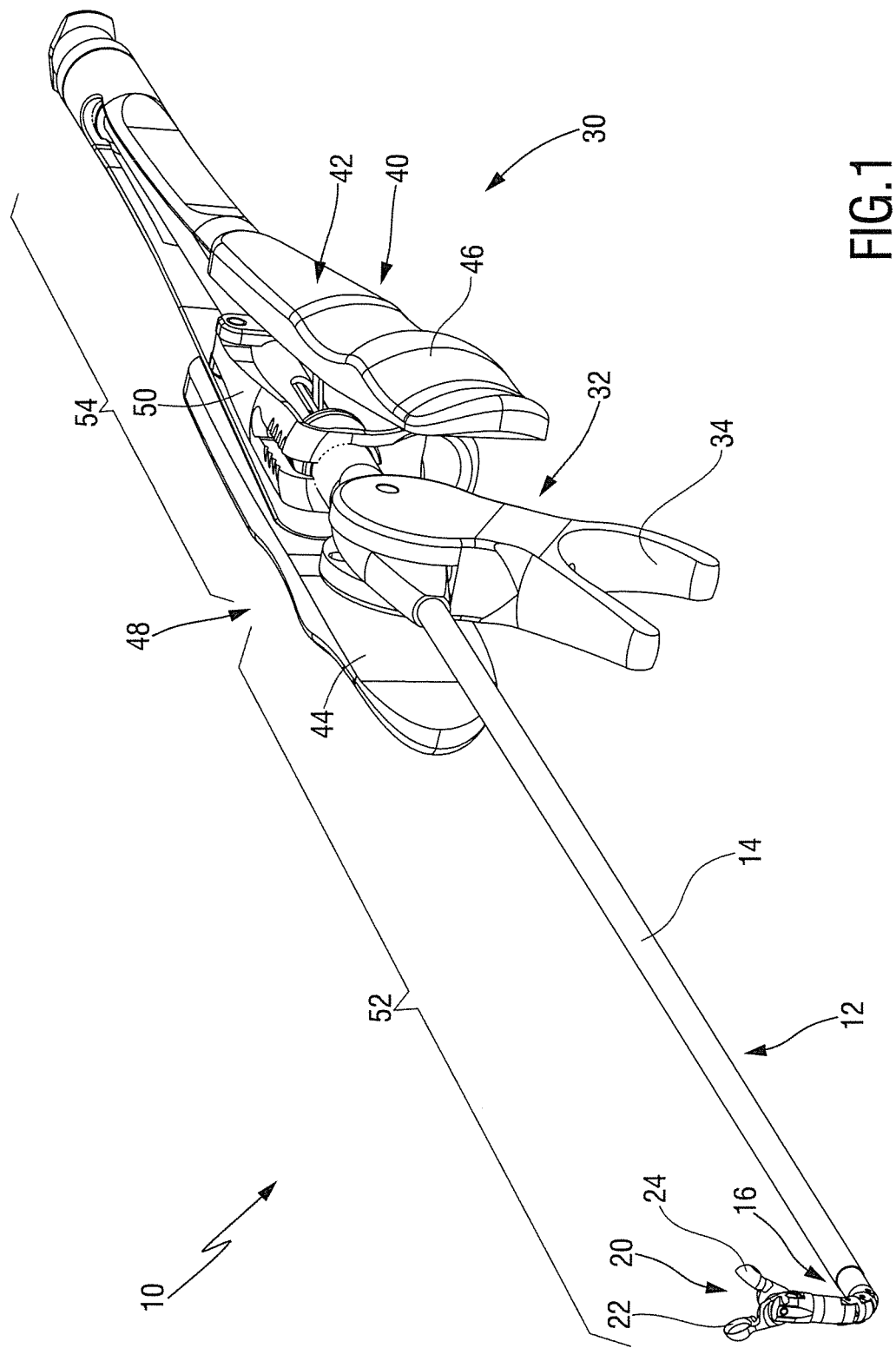
FIG. 1 is a perspective view of a neurosurgical instrument, seen from the distal end.

FIG. 1 shows with reference to a perspective representation of an exemplary embodiment of an instrument 10 whose distal end is facing the viewer and whose proximal end is facing away from the viewer. Instrument 10 is arranged as an Instrument for neurosurgery and/or brain surgery. Accordingly, the instrument 10 may also be referred to as a neurosurgical instrument.

The instrument 10 comprises a shaft 12, which is formed at least sectionally by a rigid tube 14. The tube 14 defines a longitudinal axis of the shaft 12, which extends from a proximal end to a distal end. In the region of the distal end, an articulation section 16 is associated with the shaft 12, which is shown in FIG. 1, by way of example, in a deflected and/or angled position. Furthermore, an effector 20, which is designed as a gripper, is mounted at the distal end of the shaft 12. The effector 20 comprises a first jaw part 22 and a second jaw part 24. The effector 20 is shown in FIG. 1 in an open position in which the jaw parts 22, 24 are open.

A handling portion 30, where the instrument 10 can be picked up and guided by a user, such as a surgeon or surgeon, adjoins the proximal end of the shaft 12. The shaft 12 defines a distal portion of the instrument. The handling portion 30 defines a proximal portion of the instrument 10.

The instrument 10 further comprises a deflection mechanism 32 for controlling the deflection and/or angular position of the articulation section 16. By way of example, the deflection mechanism 32 is provided with a control lever 34. The instrument 10 also comprises an actuation mechanism 40 for the effector 20. The actuation mechanism 40 comprises a handle 42 having a first arm 44 and a second arm 46. The arms 44, 46 extend distally from a proximal end of the handling portion 30 towards the shaft 12.

The instrument 10 further comprises an interface 48 to which a locking bracket 50 is associated. At the interface 48, the instrument 10 can be dismantled in a 52 shaft assembly and 54 handle. The shaft assembly 52 is a distal assembly. The handle piece 54 designates a proximal assembly. The shaft assembly 52 is associated with the shaft 12, at least sectionally. The handle piece 54 is associated with the handling portion 30, at least sectionally. In accordance with the exemplary embodiment shown in FIG. 1, at least the deflection mechanism 32, for instance the control lever 34, is associated with the shaft assembly 52, i.e. arranged distally from the interface 48. Other designs and allocations are conceivable for the deflection mechanism 32 and/or the actuation mechanism 40.

The locking bracket 50 is arranged to interlock the shaft assembly 52 and the handle piece 54. The locking bracket 50 can be pivoted to allow the shaft assembly 52 to be released from the handle piece 54.

In addition, reference is made to FIGS. 2, 3, 4 and 5. FIG. 1, FIG. 2 and FIG. 4 show that the handle 42 of the actuation mechanism 40 is accommodated at a distal end of the handle piece 54, whereas the arms 44, 46 can be deflected. The arms 44, 46 extend at least sectionally laterally from the locking bracket 50 and the control lever 34 of the deflection mechanism 32. In other words, the locking bracket 50 and the control lever 34 are arranged, at least sectionally, between the arms 44, 46 of the handle 42. Overall, this provides for good ergonomics and a clear field of vision for the operating surgeon. In addition, the configuration shown in FIG. 1 allows for easy handling. In specific embodiments, the instrument 10 further comprises an advantageous center of gravity, which makes it easier to hold and guide the instrument 10.

FIGS. 2 and 4 show broken side views of the instrument 10 that is illustrated in a perspective view in FIG. 1. FIG. 2 shows a first pivot state. FIG. 4 shows a second pivot state. FIG. 3 shows an enlarged representation of a distal region of the shaft 12 of the instrument 10, wherein the pivoting state of the articulation section 16 corresponds to the state shown in FIG. 2. FIG. 5 shows an enlarged view of the distal end of the shaft, wherein the state of the articulation section 16 shown in FIG. 5 corresponds to the pivoting state shown in FIG. 4.

FIGS. 2 and 4 show that the control lever 34 of the deflection mechanism 32 can be pivoted in order to move the articulation section 16 between a first bending state (FIG. 2) and a second bending state (FIG. 4). FIG. 2 shows a state in which the articulation section 16 is centered and concentrically oriented in relation to the longitudinal axis of the shaft 12. FIG. 5 shows a state in which the articulation section 16 is maximally deflected or angled.

The first pivoting state shown in FIG. 2 and FIG. 3 is illustrated in more detail in FIGS. 6, 7 and 8. The second bending state shown in FIGS. 4 and 5 is illustrated in more detail in FIGS. 9, 10 and 11.

FIG. 6 and FIG. 9 elucidate the pivotability of the control lever 34. FIG. 7 and FIG. 10 show corresponding cross-sectional views. FIG. 8 shows a cross-section through the articulation section 16 in the first bending state. FIG. 11 shows a cross-section through the articulation section 16 in the second bending state.

FIG. 6 and FIG. 7 illustrate that the deflection mechanism 32 further comprises a control unit 58 to which the control lever 34 is associated. The control lever 34 may be pivotably mounted on a bearing part 60. A pivot axis 62 for the control lever 34 is indicated in FIG. 6 and FIG. 9 by 62. When moving between the states shown in FIG. 6 and FIG. 9, the control lever 34 is pivoted about the pivot axis 62.

With additional reference to FIG. 7 and FIG. 10, the control lever 34 is, in accordance with exemplary embodiments, provided with adjusting screws 66, 68, which enable a fine tuning and/or adjustment of the angular positions of the control lever 34 in relation to the bearing support 60. FIG. 7 shows the control unit 58 in a state in which the articulation section 16 is in the first bending state, refer also to FIG. 8. In this state, the adjusting screw 66 may contact the bearing part 60 and provide an adjustable limit stop for the control lever 34.

FIG. 10, on the other hand, illustrates a second state of the control lever 34, which corresponds to the second bending state of articulation section 16 shown in FIG. 11. In the second state of the control lever 34, the adjusting screw 68 contacts the bearing part 60. Accordingly, an adjustable stop is also available in the second state, which can be used to fine tune and/or to adjust the pivot state of the control lever 34 in relation to the bearing part 60.

FIGS. 7 and 10 further show that the control lever 34 and the bearing part 60 are mutually connected via slide pieces 72, 74. A first slide piece 72 is associated with a first pull element 76. A second slide piece 74 is associated with a second pull element 78, refer also to FIG. 8 and FIG. 11.

The slide piece 72 is connected to the pull element 76 at a proximal end of the pull element 76 for movement entrainment. The slide piece 74 is connected to the pull element 78 at a proximal end of the pull element 78 for movement entrainment.

The pull element 76 is arranged, by way of example, as a pull wire 80. The pull element 78 is arranged, by way of example, as a pull wire 82. The pull elements 76, 78 are, in specific embodiments, made of a highly elastic material. This may involve, for instance, nitinol and/or a similar superelastic alloy.

By way of example, the curved illustration in FIG. 11 shows that the first pull element 76 may also be referred to as an inner pull element. The pull element 78 may also be referred to as an outer pull element, in regard of the respective radius of curvature of pull elements 76, 78. Accordingly, the pull wire 80 can also be referred to as an inner pull wire. The pull wire 82 may also be referred to as the outer pull wire. The articulation section 16 may be deflected and/or angled by pulling the pull element 76 distally, refer to FIG. 11. By pulling the pull element 78, the articulation section 16 can be folded in or returned to its starting position, which corresponds approximately to a central position, refer also to FIG. 8.

In this way, pivoting the control lever 34 towards the distal end of the instrument 10 causes the articulation section 16 to deflect into an angled position. Conversely, a swiveling movement of the control lever 34 towards the proximal end of the instrument 10 generates a pull on the tensioning element 78. In this way, the articulated section 16 is caused to be moved from the curved position back to the straight, central position.

The articulation section 16 is elucidated in more detail with reference to FIG. 8 and FIG. 11. The articulation section 16 comprises, for instance, an articulated link 88 and an articulated link 90, which are arranged between a proximal connector piece 92 and a distal connector piece 94. Pivot axes 96, 98, 100 illustrate that in this embodiment the arrangement comprising the connector piece 92, the articulated link 88, the articulated link 90 and the connector piece 94 can be pivoted altogether, respectively involving a relative pivoting of adjacent links.

In specific embodiments, the articulated links 88, 90 and, in certain embodiments, also the connector pieces 92, 94 are provided with limit stops 106, 108, 110, 112. FIG. 8 shows, by way of example, limit stops 106, 108 which are opposite to each other, wherein the limit stop 106 is associated with the articulated link 88 and the limit stop 108 with the articulated link 90. It goes without saying that there are other limit stops on this side. FIG. 11 shows that in the curved state of the articulation section 16, the limit stops 106, 108 contact each other.

Similarly, FIG. 11 shows that further limit stops 110 and 112 are provided, which define a straight, elongated orientation of the articulation section 16. The limit stop 110 is associated with the articulated link 88. The limit stop 112 is associated with the articulated link 90. Other links involved are similarly provided with limit stops. A comparison between FIG. 8 and FIG. 11 shows that the stops 110, 112 are used to define the straight, central orientation of articulation section 16. At least the central position of articulation section 16 is defined by the stops 110, 112, with high precision and repeatable.

Similarly, the limit stops 106, 108 may be arranged to ensure high position accuracy and repeatability also for the angled/deflected stayed of the articulation section 16.

The exemplary embodiment shown in FIG. 8 and FIG. 11 also illustrates that the pull elements 76, 78 are used to pivot and/or return the articulated section 16. However, the actual positioning in the respective end positions is provided by means of the limit stops 106, 108 for the position shown in FIG. 11, and the limit stops 110, 112 for the position shown in FIG. 8.

Figure 12:
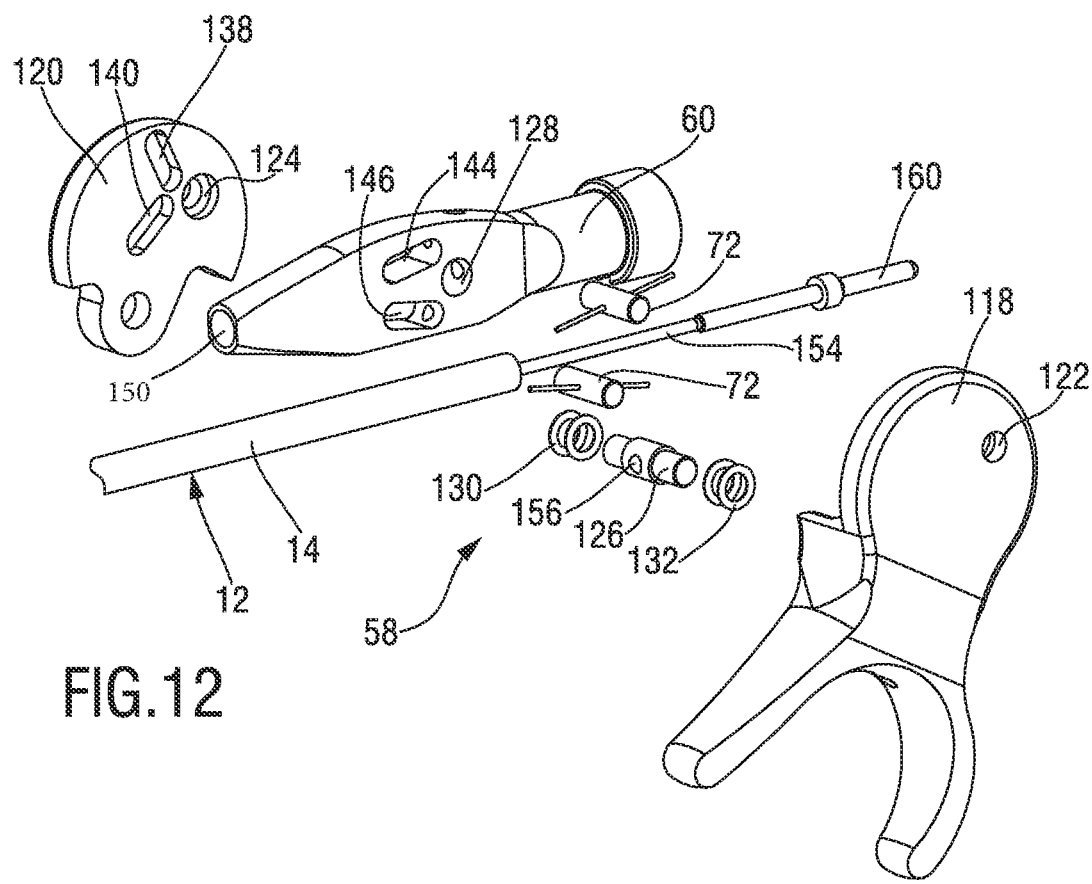
FIG. 12 is a perspective exploded partial view of a control unit for a deflection mechanism of an instrument.
Figure 13:
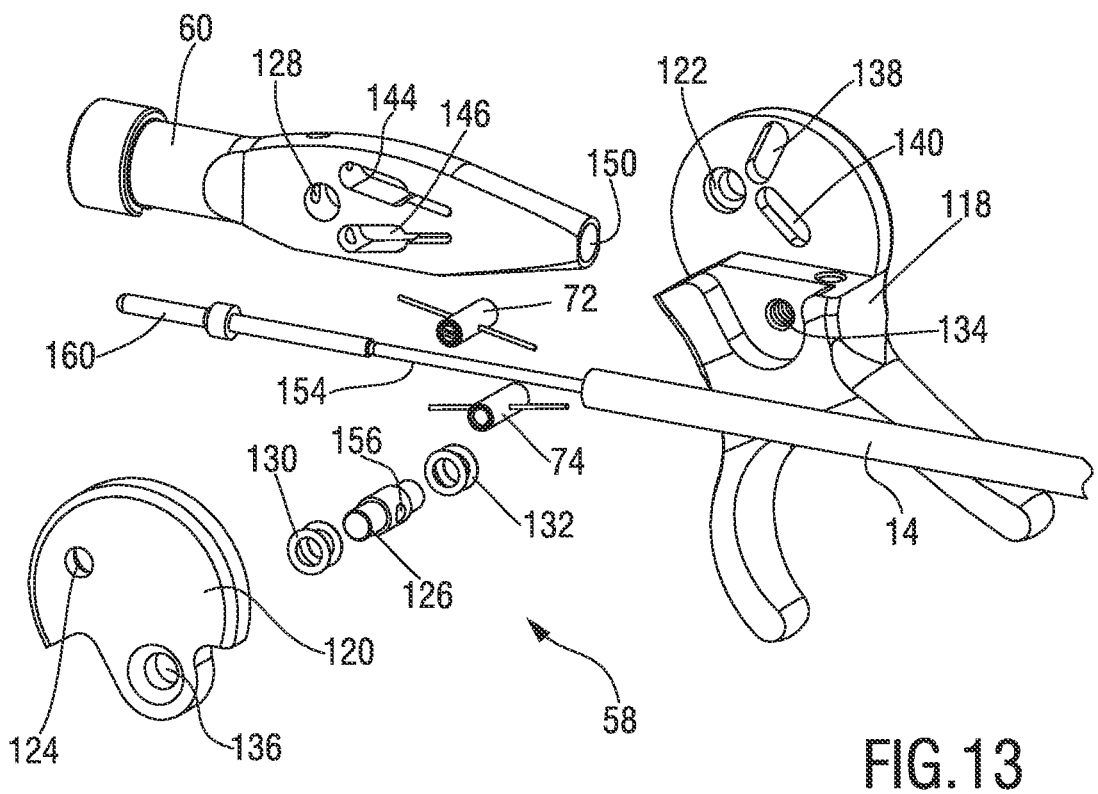
FIG. 13 is another perspective exploded representation of the control unit according to FIG. 12 in a different orientation from that shown in FIG. 12.

With reference to FIG. 12 and FIG. 13, an exemplary embodiment of the control unit 58 for the deflection mechanism 32 is further illustrated. FIG. 12 and FIG. 13 each show exploded perspective views, wherein the views are based on different orientations.

By way of example, the control lever 34 is formed in two parts and comprises a first side part 118 and a second side part 120. The side parts 118, 120 may be screwed together. The first side part 118 is provided with a bearing recess 122. The second side part 120 is provided with a bearing recess 124.

For the pivotable mounting of the control lever 34 there is provided a bearing pin 126, which can be accommodated in a bearing recess 128 on the bearing part 60. The side part 118 is arranged via the bearing recess 122 on the bearing pin 126. The side part 120 is arranged via the bearing recess 124 on the bearing pin 126. Accordingly, the control lever 34, which comprises the side parts 118, 120, may be pivoted about the bearing pin 126.

It goes without saying that the bearing pin 126 may also be integrally formed at the bearing part 60. In accordance with this exemplary embodiment, no separate bearing recess 128 is provided for the bearing part 60.

Further, in FIGS. 12 and 13, elastic clamping bodies indicated by 130, 132, which are intended to increase friction and/or to secure the position. The clamping bodies 130, 132 may be arranged as so-called O-rings for instance. FIGS. 12 and 13 show that two clamping bodies 130, 132 are associated with each lateral end of the bearing pin 126. The clamping body(s) 130 is/are disposed between the bearing pin 126 and the bearing recess 122. The clamping body(s) 132 is/are disposed between the bearing pin 126 and the bearing recess 124. The side parts 118, 120 of the control lever 34 are also provided with mounting openings 134, 136. The mounting opening 134 provided on the side part 118 includes a thread, for instance. The mounting opening 136 provided on the side part 120 includes a through hole for a screw, for instance.

In an assembled state, the control lever 34 may be pivoted about the bearing pin 126, whereas the clamping bodies 130, 132 cause an increase in friction which may result in a self-locking or position lock. In other words, it is preferred that the control lever 34 maintains its actual pivot position relative to the bearing part 60 automatically and without external influence. The corresponding frictional forces are generated primarily by the clamping bodies 130, 132, which are accommodated with preloading between the bearing part 60 and the side part 118 as well as between the bearing part 60 and the side part 120.

Figure 14:
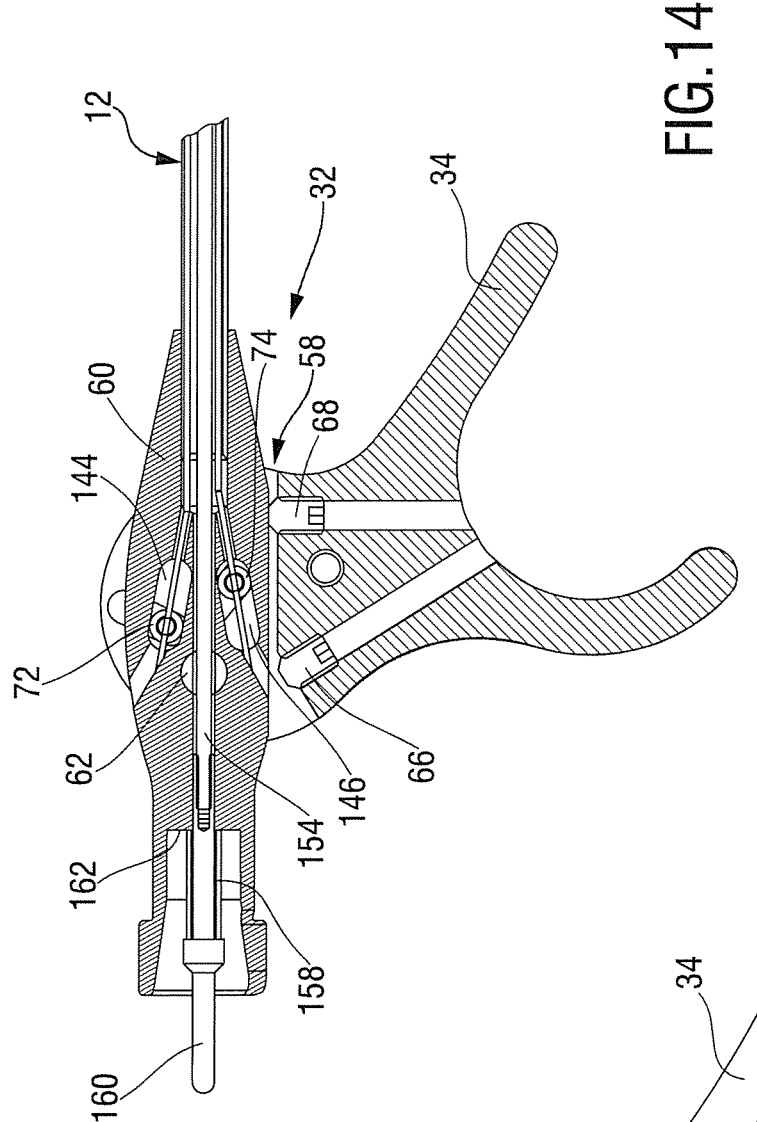
FIG. 14 is an enlarged cross-sectional view of a control unit of a deflection mechanism for an instrument in a state similar to that shown in FIGS. 9, 10 and 11.
Figure 15:
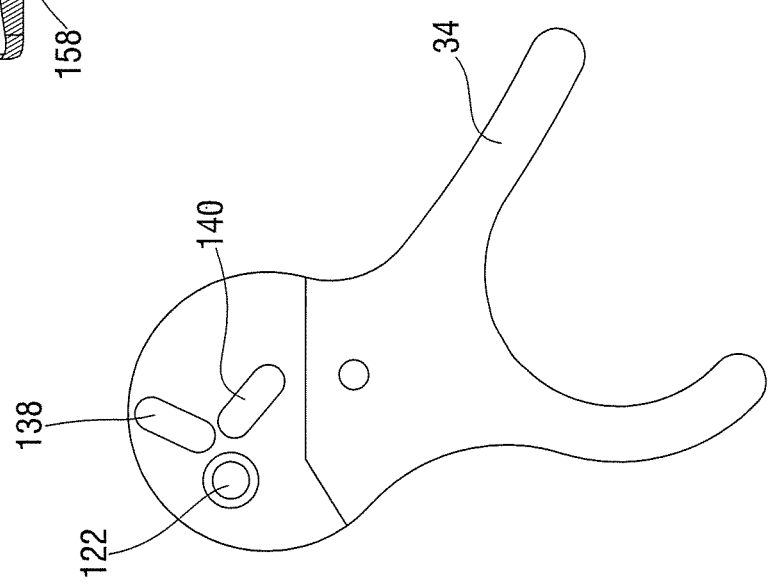
FIG. 15 is an isolated view of a control lever for the control unit shown in FIG. 14.

In addition to FIGS. 12 and 13, further reference is made to FIGS. 14 and 15. FIG. 14 shows a cross-sectional view of the control unit 58 for the deflection mechanism 32. FIG. 15 shows an isolated side view of a control lever 34.

A first guideway 138 and a second guideway 140 are formed on the control lever 34. In addition, particularly FIG. 12 and FIG. 13 show that a first guideway 144 and a second guideway 146 are formed on the bearing part 60.

The slide piece 72 for the first pull element 76 is mounted in the assembled state in the guideway 144 of the bearing part 60 and the guideway 138 of the control lever 34. The slide piece 74, which is associated with the pull element 78, is mounted in the guideway 146 of the bearing part 60 and the guideway 140 of the control lever 34.

When the control lever 34 swivels about the pivot axis 62 (refer also to FIG. 6 and FIG. 9), the guideways 138, 140 are used to drive the slide pieces 72, 74, refer also to FIG. 15. The slide pieces 72, 74 are coupled with the pull elements 76, 78. In this way, at the distal end of the instrument the articulation section 16 can be straightened or angled.

FIG. 15 shows that the guideways 138, 140 at the control lever 34 are mounted in a defined way relative to the bearing recess 122, 124. As a result, when the control lever 34 is pivoted about the pivot axis 62, the pull elements 76, 78 are not moved by the same amount. This measure has the effect that different bending radii of the pull elements 76, 78 can be compensated, refer also to FIG. 11.

A further goal of the arrangement of the control unit 58 elucidated with reference to FIGS. 12 to 15 is that, if possible, both pull elements 76, 78 are simultaneously subjected to tensile stress when the control lever 34 is pivoted to proximally or distally. As already explained above in connection with FIG. 8 and FIG. 11, it is generally sufficient to pull the first pull element 76 for deflection/angulation. Conversely, it is sufficient to move the second pull element 78 distally in order to move the articulation section 16 back to a straightened, central position.

In accordance with exemplary aspects of the present exemplary embodiment, the control unit 58 is formed in such a way that both pull elements 76, 78 are at least slightly pretensioned in their longitudinal extension. This has the effect that the deflection mechanism 32 provides low backlash or almost zero backlash. This prevents excessive play, for instance when reversing the movement.

In the bearing part 60, a passage 150 extends between a distal and a proximal end. By way of example, the passage 150 is concentrically in relation to a longitudinal axis through the shaft 12. FIG. 14 shows a state of instrument 10 in which the shaft 12 and the bearing support 60 are assembled, whereas a push piece 154 is arranged in the shaft 12, which extends through the passage 156 in the bearing pin 126.

FIG. 12, FIG. 13 and FIG. 14 further illustrate that in addition to the pull elements 76, 78, also the push piece 154 is arranged at the shaft 12, for instance in the tube 14. A passage 156 is provided on the bearing pin 126 for the push piece 154, so that it can be led centrally through the bearing pin 126.

At the proximal end of the push piece 154, a pressure piece 160 is provided, which is connected to the push piece 154. Further, in FIG. 14, a compression spring or spring is indicated with 158, which is arranged between the pressure piece 160 and a limit stop 162 on the bearing part 60 in order to urge the push piece 154 towards the proximal end. This may also contribute to the low backlash or even zero backlash design of the control unit 58 and the deflection mechanism 32. In certain embodiments, the pressure piece 160 is arranged as a plunger.

Additional reference is made to FIGS. 16, 17 and 18 as well as to FIGS. 19, 20 and 21. FIG. 16, FIG. 17 and FIG. 18 show an effector 20 mounted on the distal end of the shaft, which is designed as a gripper 164, for instance. It goes without saying that the effector 20 may alternatively be designed as pliers, pincers, scissors, a clamp and in a similar way.

FIG. 19, FIG. 20 and FIG. 21 show the effector 20 in an open position. FIG. 16, FIG. 17 and FIG. 18 show the Effector 20 in a closed position. FIG. 19 corresponds with FIG. 16, FIG. 20 corresponds with FIG. 17. FIG. 21 corresponds with FIG. 18.

At the connector piece 94, which is coupled with at least one articulated link 88, 90 (refer to FIG. 8 and FIG. 11), a head piece 166 is mounted, which is designed as clevis 168, by way of example. The head piece 166 comprises a first side piece 170 and a second side piece 172. A coupling piece 174 is slidably mounted between the side pieces 170 and 172, the coupling piece 174 comprising a flat portion 176 at its distal end. A driver 178 and a further driver 180 extend from the flat portion 176. The drivers 178, 180 are mounted on opposite sides of the flat portion 176.

The coupling piece 174 is coupled with the first jaw part 22 and the second jaw part 24 via the drivers 178, 180. For this purpose, the first jaw part 22 is provided with a driving recess 186. In addition. A second driving recess 188 is provided at the second jaw part 24. In the mounted state of the instrument 10, the driver 178 engages the driving recess 186 on the jaw part 22. Accordingly, the driver 180 engages the driving recess 188 on the second jaw part 24.

Further, the first jaw part 22 has a projection 194. In addition, the second jaw part 24 has a projection 196. The first projection 194 is associated with a bearing recess 198 on the head piece 166. The second projection 196 is associated with a bearing recess 200 at the head piece 166. The projection 194 extends from a flat portion 202 of the first jaw part 22. The projection 196 extends from a flat portion 204 of the second jaw part 24.

A guideway 206 is formed at the flat portion 202. A guideway 208 is formed at the flat section 204. In the assembled state of the effector 20 and an actuation mechanism 40 for the effector 20, there is further provided a guide pin 214, which extends through a guide recess 216 in the flat part 176 of the head piece 166. The guide pin 214 is mounted on a seat 222 on the side part 170 and a seat 224 on the side part 172. Between the side parts 170, 172 the coupling piece 174 as well as the first jaw part 22 and the second jaw part 24 are arranged, for instance via their flat portions 176, 202, 204 The flat portion 176 of the coupling piece 174 is arranged between the flat portions 202, 204 of the jaw parts 22, 24. The guide pin 214, which extends between the seats 222, 224, also projects through the guideway 206 on the first jaw part 22, the guideway 208 on jaw part 24 and the guide recess 216 in the flat portion 176 of coupling piece 174.

A comparison of FIG. 16, FIG. 17 and FIG. 18 with FIG. 19, FIG. 20 and FIG. 21 shows that the coupling piece 174 is pushed distally to close the jaw parts 22, 24. When the coupling piece 174 is pushed or displaced proximally, the jaw parts 22, 24 are opened.

The push piece 154 already described above in connection with FIGS. 12, 13 and 14 is connected to the coupling piece 174 in order to move it to close or open the effector 20.

Generally, the push piece 154 may also be made of a highly elastic material or even of a superelastic alloy, such as nitinol.

With additional reference to FIG. 22 and FIG. 23, the actuation mechanism 40 for the effector 20 is illustrated in more detail. As already explained in connection with FIG. 1, the handle 42 of the actuation mechanism 40 is arranged at the distal end of the instrument 10. The handle 42 is mounted on a support shaft 228, which is connected in series with the bearing part 60 and the shaft 12. In FIG. 23, the bearing part 60 and the support shaft 228 are omitted for illustrative purposes. Furthermore, the arms 44, 46 of the handle 42 are not explicitly shown in FIGS. 22 and 23 (refer to FIG. 1 in this context). The arms 44, 46 are formed as attachment parts.

The actuation mechanism 40 comprises a coupling mechanism 230 comprising a pushing slider 232 that can be coupled to the pressure piece 160, which is provided at the proximal end of the push piece 154. The slider 232 comprises a cup-shaped seat 234 and an adjoining flat portion 236. The slider 232 may be attached onto the pressure piece 160 in order to push it towards the distal end of the instrument. An opposite force is generated by the spring 158, which is indicated in FIG. 23. The installed state of the spring is depicted in the illustration in FIG. 14, refer also to FIG. 26.

The handle 42 comprises actuation sections 238, 240, which extend approximately from proximal to distal in a pincer-shaped manner. The support shaft 228 extends between the actuation sections 238, 240, and the handle 42 is attached to its distal end.

The actuating section 238 is coupled via a coupling element 246 to the flat portion 236 of the cup-shaped slider 232. The actuation section 240 is connected to the flat portion 236 via a coupling member 248. The coupling members 246, 248 have the same pivot point at the flat portion 238 of the slider 232. When the two actuation sections 238, 240 of the handle 42 are moved towards each other, i.e. pressed together, the coupling elements 246, 248 urge the slider 232 against the pressure piece 160 in order to move the push piece 154 towards the distal end of the instrument 10. This causes the jaw parts 22, 24 of the Effector 20 to close.

The coupling member 246 is articulatedly mounted via a bearing pin 254 at the actuation section 238. The coupling member 248 is articulatedly mounted at the actuation section 240 via a bearing pin 256. The coupling members 246, 248 extend through passages 250, which are formed in the support shaft 228, cf. also the illustration of the support shaft 228 with the passage 250 in FIG. 25.

An articulation section 262 is formed at actuation section 238. An articulation section 264 is formed at actuating section 240, refer to FIG. 22 The articulating sections 262, 264 may, for instance, have a material weakening in order to provide a living hinge swivel joint and/or a virtual pivot point and/or a virtual pivot axis for actuating sections 238, 240.

Also the actuating mechanism 40 for the effector 20 is arranged to have little or even no backlash. At the proximal end of the push piece 154 there is formed the pressure piece 160, which is urged towards the proximal end of the instrument by the spring 158. From the distal end, the coupling mechanism 230 acts via the slider 232 on the pressure piece 160 and presses it opposed to the force of the spring 158 towards the proximal end of the instrument 10 when the actuation sections 238, 240 are moved towards each other. Provided that also the coupling mechanism 230 acts at least with a slight pretension on the pressure piece 160, the latter may be "floatingly" disposed with little or no backlash between the coupling mechanism 230 and the spring 158. For this purpose, it is conceivable to form the actuation sections 238, 240 of the handle 42 with a certain preloading. In other words, the coupling mechanism 230 may be designed in such a way that the actuation sections 238, 240 are pushed inwardly even in an externally unloaded state, thus generating a preloading force on the slider 232.

With reference to FIG. 24 and FIG. 25, and with additional reference to FIG. 26 and FIG. 27, an exemplary embodiment of the interface 48 between the shaft assembly 52 and the handle piece 54 is Illustrated in more detail. The interface 48 may be locked or unlocked via a locking bracket 50.

The interface comprises a male mating part 270 and a female mating part 272. The male mating part 270 may also be referred to as an internal part. The female mating part 272 may also be referred to as an outer part. The male mating part 270 can be inserted into the female mating part 272 to align the shaft assembly 52 and the handle piece 54 with each other. A retaining portion 276 is formed on the female mating part 272, for instance in the form of a step or a shoulder. The locking bracket 50 comprises a retaining arm 278 at its distal end, refer to the illustration in FIG. 25, which shows the locking bracket 50 in an isolated form.

The locking bracket 50 may engage the retaining portion 276 via the retaining arm 278 in order to lock the assembled state of the male mating part 270 with the female mating part 272.

The retaining arm 278 includes, by way of example, a position securing section 280, which is followed by a release section 282, refer again to FIG. 25 The position securing section 280 comprises a constriction. The release section 282 includes a widening. Together, the position securing section 280 and the release section 282 may form a keyhole contour. The locking bracket 50 is pivotably mounted on a bearing part 286 by means of a hinge 288. The bearing part 286 is arranged on the support shaft 228.

Depending on the current pivoting state of the locking bracket, the position securing section 280 or the release section 282 is aligned with the retaining portion 276. For an assembly movement (or disassembly movement), the locking bracket 50 is pivoted in such a way that the release section 282 is essentially concentric to the support shaft 228 and the male mating part 270, respectively. The male mating part 270 may then be joined with the female mating part 272, refer also to the state in FIG. 26.

Thereafter, the locking bracket 50 may be pivoted in such a way that the position securing section 280 engages the retaining portion 276 in order to secure the assembled condition between the male mating part 270 and the female mating part 272. To unlock the interface 48, an opposite movement can be applied to the locking bracket 50 in order to guide the position securing section 280 out of the locked state at retaining portion 276. It is conceivable to mount the locking bracket 50 on the support shaft 228 in such a way that a pretensioning towards the locked state results. This may further increase safety. The risk of incorrect actuation may be reduced.

By way of example, the position securing section 280 on the retaining arm 278 of the locking bracket 50 is arranged in such a way that it is only possible to disengage from the support section 276 by elastic deformation, e.g. by lateral expansion, of the locking bracket 50 in the region of the retaining arm 278. In this way, a certain force must be applied in order to disengage the position securing section 280 and to bring the release section 282, which has a larger cross-section, in alignment with the retaining portion 276. Furthermore, it is conceivable to form a recess 290 on a back side of the locking bracket 50, which ends in the position securing section 280. In this way, a defined deformability of the retaining arm 278 in the area of the position securing section 280 is provided.

In order to secure a relative rotational position between the shaft assembly 52 and the handle piece 54, a groove 292 is formed on the female mating part 272, for instance. The groove 292 extends axially and is open at its proximal end. A guide pin 294 is arranged on the male mating part 270, which is oriented radially to a longitudinal axis of the instrument 10. When joining the male mating part 270 with the female mating part 272, the guide pin 294 may engage the groove 292 to secure the desired rotational position.

The cross-sectional illustrations in FIG. 26 and FIG. 27 illustrate that a conical surface 300 is formed on the male mating part 270, which is adjoined by a cylindrical surface 304. A conical surface 302 is formed on the female mating part 272, which is adjoined by a cylindrical surface 306. The conical surface 302 and the cylindrical surface 306 are inner surfaces. The conical surface 300 and the cylindrical surface 304 are outer surfaces. In the assembled state, a defined axial and concentric alignment between the shaft assembly 52 and the handle piece 54 results, involving low backlash or even no backlash. A relative rotational orientation between the shaft assembly 52 and the handle piece 54 is defined by the groove 292 and the guide pin 294.

However, it is also conceivable to dispense with the conical surfaces 300, 302. Accordingly, the mating parts 270, 272 may be primarily provided with cylindrical surfaces 304, 306 which ensure a concentric alignment.

FIG. 26 and FIG. 27 further illustrate that the interface 48 also includes the pressure piece 160 on the part of the shaft assembly 52 and the slider 232 on the part of the handle piece 54. A sliding movement may be transferred to the pressure piece 160 via the slider 232, in order to displace the push piece 154 towards the distal end of the instrument, in order to control the effector 20. Via the slider 232, primarily pressure forces are transmitted to the pressure piece 160.

Accordingly, a connection may be created by simply attaching the slider 232 onto the pressure piece 160. A resetting movement or restoring force is caused by the spring 158, which is arranged between the pressure piece 160 and the bearing part 60, whereby the spring 158 is concentrically aligned with the longitudinal axis of the instrument 10. Hence, motion transmission for the degree of freedom of movement of the effector 20 is also arranged to involve low backlash or even no backlash.

What is claimed is:

1. A surgical instrument, comprising:
    a shaft extending between a distal end and a proximal end, wherein a deflectable articulation section is formed at the shaft,
    a proximal handling portion at the proximal end of the shaft,
    a distal effector at the distal end of the shaft, and
    a deflection mechanism for controlling a bending state of the articulation section, the deflection mechanism comprising a first pull element and a second pull element, wherein the first pull element and the second pull element are at least sectionally jointly pretensioned during the movement of the articulation section;
    wherein the first pull element is formed as a first pull wire and the second pull element is formed as a second pull wire that are arranged on opposite sides of a central axis of the shaft;
    wherein the pull elements each extend between a proximal coupling point and a distal coupling point in the shaft, and wherein the pull elements are each coupled at their proximal end with a control unit that comprises a pivotable control lever; and
    wherein the control unit comprises at the control lever a first guideway for the first pull element and a second guideway for the second pull element, wherein at the handling portion a first stationary guideway for the first pull element and a second stationary guideway for the second pull element is provided, wherein the first stationary guideway and the second stationary guideway at the handling portion are each inclined with respect to a longitudinal axis of the shaft, wherein the first pull element is coupled with the first stationary guideway at the handling portion and the first guideway of the control lever, and wherein the second pull element is coupled with the second stationary guideway at the handling portion and the second guideway of the control lever.

2. The instrument as claimed in claim 1, wherein the first pull element and the second pull element are simultaneously subjected to tensile stress, in the same direction, when the articulation section is swiveled out or swiveled in.

3. The instrument as claimed in claim 1, wherein the guideways for the first pull element and the second pull element are arranged for compensating a length offset between the first pull element and the second pull element that is caused by different bending radii of the first pull element and the second pull element during the deflection and return of the deflection mechanism.

4. The instrument as claimed in claim 1, wherein the guideways for the first pull element and the second pull element are arranged such that when alternating between two bending states both pull elements are at least sectionally simultaneously subjected to tension when the control lever is pivoted.

5. The instrument as claimed in claim 1, wherein the pull elements are made from a superelastic alloy.

6. The instrument as claimed in claim 1, wherein the articulation section comprises a plurality of articulated links that are articulatedly connected in a series with each other, wherein the articulated links are provided with limit stops for defining at least one bending state without play, and wherein the limit stops of adjacent articulated links contact each other in a first state of the shaft and are spaced away from one another in a second state of the shaft.

7. The instrument as claimed in claim 6, wherein the first state is a straight, undeflected state in which the shaft is in the central position, and wherein the second state is a deflected state of the shaft.

8. The instrument as claimed in claim 1, wherein at least one friction increasing elastic clamping body is provided that secures the actual bending state of the shaft.

9. A surgical instrument, comprising:
    a shaft extending between a distal end and a proximal end, wherein a deflectable articulation section is formed at the shaft,
    a proximal handling portion at the proximal end of the shaft,
    a distal effector at the distal end of the shaft, and
    an interface where the instrument is demountable into a distal shaft assembly and a proximal handle piece, wherein the effector is controlled via an actuation mechanism that comprises a push piece, and that passes through the interface in a mounted state;

wherein a locking bracket cooperates with the interface, the locking bracket being arranged to engage a retaining portion to secure an axial relative position between the shaft assembly and the handle piece, wherein the locking bracket is articulatedly arranged at the handle piece, and wherein the retaining portion is formed at the shaft assembly; and wherein the locking bracket is flexible and deformable to engage with and disengage from the retaining portion.

10. The instrument as claimed in claim 9, wherein the interface comprises mating parts that comprise a male part and a female part that can be coupled with one another.

11. The instrument as claimed in claim 9, wherein at the locking bracket a retaining arm is formed that at least sectionally encompasses the retaining portion, wherein the retaining arm comprises a position securing section and a widened release section, and wherein the retaining arm is formed on a distal end of the locking bracket.

12. The instrument as claimed in claim 9, wherein the interface further comprises a rotary position lock arranged as a guide pin that engages an axially extending groove.

13. The instrument as claimed in claim 12, wherein the actuation mechanism comprises at the interface a releasable coupling between a pressure piece at the proximal end of a push piece on the part of the shaft assembly for controlling the effector, and a slider on the part of the handle piece for applying force to the pressure piece to actuate the effector in a connected state of the interface.

14. A surgical instrument, comprising:
a shaft extending between a distal end and a proximal end, wherein a deflectable articulation section is formed at the shaft,
a proximal handling portion at the proximal end of the shaft, and
a distal effector at the distal end of the shaft,
wherein the effector is controlled via an actuation mechanism that comprises a push piece having a distal end that is coupled with the effector and a proximal end that is actuable by a pushing movement;
wherein the effector comprises a first jaw part and a second jaw part that are pivotable with respect to one another when the push piece is displaced; and
wherein the push piece is connected at a distal end thereof with a coupling piece that comprises a first driver for the first jaw part and a second driver for the second jaw part, wherein the first jaw part comprises a driving recess, wherein the second jaw part comprises a driving recess, wherein the first driver of the coupling piece engages the driving recess of the first jaw part, and wherein the second driver of the coupling piece engages the driving recess of the second jaw part.

15. The instrument as claimed in claim 14, wherein the push piece is displaced distally to move the first jaw part and the second jaw part towards each other for closing.

16. The instrument as claimed in claim 14, further comprising a head piece at the distal end of the shaft, wherein the first jaw part is pivotably mounted at the head piece, wherein the second jaw part is pivotably mounted at the head piece, and wherein pivot axes of the first jaw part and the second jaw part are parallel to and spaced away from one another.

17. The instrument as claimed in claim 16, wherein the first jaw part comprises a first guideway, wherein the second jaw part comprises a second guideway, and wherein a guide pin that is arranged at the head piece engages the first guideway and the second guideway.

18. The instrument as claimed in claim 17, wherein the coupling piece extends at least sectionally between the first jaw part and the second jaw part, and wherein the guide pin extends through a recess of the coupling piece.

19. The instrument as claimed in claim 14, wherein at the proximal end of the push piece a pressure piece is provided that can be coupled with a slider, wherein the slider is mounted at the handling portion in a longitudinally displaceable manner, and wherein the slider is coupled with an actuating handle that comprises at least one actuating section that is pivotably accommodated at the handling portion.

20. The instrument as claimed in claim 19, wherein the actuating handle, the slider and at least one coupling member form a coupling mechanism at the handling portion, and wherein a pivoting movement of the at least one actuating section is transferred to a pushing movement of the slider.

21. A surgical instrument, comprising:
a shaft extending between a distal end and a proximal end, wherein a deflectable articulation section is formed at the shaft,
a proximal handling portion at the proximal end of the shaft, and
a distal effector at the distal end of the shaft,
wherein the effector is controlled via an actuation mechanism that comprises a push piece having a distal end that is coupled with the effector and a proximal end that is actuable by a pushing movement;
wherein at the proximal end of the push piece a pressure piece is provided that can be coupled with a slider, wherein the slider is mounted at the handling portion in a longitudinally displaceable manner, and wherein the slider is coupled with an actuating handle that comprises at least one actuating section that is pivotably accommodated at the handling portion; and
wherein the actuating handle is arranged in a pincer-like manner and provided with two arms that are coupled with the actuating sections, and that are opened towards the shaft, and wherein the arms at least sectionally laterally embrace the locking bracket and the control lever.

22. The instrument as claimed in claim 21, wherein, along a main extension direction of the instrument, seen from proximal to distal, the actuating handle, the locking bracket and the control lever are successively and articulatedly arranged, wherein pivot axes of the locking bracket and the control lever are parallel to one another, and wherein the actuating handle arms are each pivotable about a pivot axis that is perpendicular to the pivot axes of the locking bracket and the control lever.

23. A surgical instrument, comprising:
a shaft extending between a distal end and a proximal end, wherein a deflectable articulation section is formed at the shaft,
a proximal handling portion at the proximal end of the shaft, and
a distal effector at the distal end of the shaft,
wherein the effector is controlled via an actuation mechanism that comprises a push piece having a distal end that is coupled with the effector and a proximal end that is actuable by a pushing movement;
wherein at the proximal end of the push piece a pressure piece is provided that can be coupled with a slider, wherein the slider is mounted at the handling portion in a longitudinally displaceable manner, and wherein the slider is coupled with an actuating handle that comprises at least one actuating section that is pivotably accommodated at the handling portion; and wherein the push piece is proximally pretensioned at the proximal end by a spring, and wherein the spring extends between the pressure piece and a distal limit stop at the handling portion.

\* \* \* \* \*